United States Patent
Nazzaro et al.

(10) Patent No.: US 11,786,668 B2
(45) Date of Patent: Oct. 17, 2023

(54) DRUG DELIVERY DEVICES, SYSTEMS, AND METHODS WITH FORCE TRANSFER ELEMENTS

(71) Applicant: Insulet Corporation, Acton, MA (US)

(72) Inventors: David Nazzaro, Groveland, MA (US); Ian McLaughlin, Boxboro, MA (US); Jeff Barnes, Medford, MA (US); Daniel Allis, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 539 days.

(21) Appl. No.: 16/140,165

(22) Filed: Sep. 24, 2018

(65) Prior Publication Data

US 2019/0091416 A1  Mar. 28, 2019

Related U.S. Application Data

(60) Provisional application No. 62/562,802, filed on Sep. 25, 2017.

(51) Int. Cl.
*A61M 5/315* (2006.01)
*A61M 5/32* (2006.01)
(Continued)

(52) U.S. Cl.
CPC ...... *A61M 5/31565* (2013.01); *A61M 5/1454* (2013.01); *A61M 5/14248* (2013.01); (Continued)

(58) Field of Classification Search
CPC .......... A61M 5/14244; A61M 5/14248; A61M 5/145; A61M 5/1452; A61M 5/1454; (Continued)

(56) References Cited

U.S. PATENT DOCUMENTS 1,441,508 A  1/1923 Marius et al.
2,198,666 A  4/1940 Gruskin
(Continued)

FOREIGN PATENT DOCUMENTS

CA  606281 A  10/1960
CN  1375338 A  10/2002
(Continued)

OTHER PUBLICATIONS

Lind, et al.,"Linear Motion Miniature Actuators." Paper presented at the 2nd Tampere International Conference on Machine Automation, Tampere, Finland (Sep. 1998), 2 pages.
(Continued)

*Primary Examiner* — Shefali D Patel
(74) *Attorney, Agent, or Firm* — GOODWIN PROCTER LLP

(57) ABSTRACT

A wearable drug delivery device that can deliver a liquid drug stored in a container to a patient is provided. The container can be a prefilled cartridge that can be loaded into the drug delivery device by the patient or that can be preloaded within the drug delivery device when provided to the patient. A sealed end of the container is pierced to couple the stored liquid drug to a needle conduit that is coupled to a needle insertion component that provides access to the patient. A drive system of the drug delivery device can expel the liquid drug from the cartridge to the patient through the needle conduit. The drive system can include a spring coupled to a plurality of force transfer elements. The force transfer elements can have a variety of shapes and configurations.

20 Claims, 22 Drawing Sheets

(51) Int. Cl.
   *A61M 5/24* (2006.01)
   *A61M 5/142* (2006.01)
   *A61M 5/145* (2006.01)

(52) U.S. Cl.
   CPC ........ *A61M 5/2455* (2013.01); *A61M 5/3287* (2013.01); *A61M 2005/14252* (2013.01); *A61M 2005/14268* (2013.01); *A61M 2005/14506* (2013.01); *A61M 2005/31518* (2013.01)

(58) Field of Classification Search
   CPC ............ A61M 5/1456; A61M 5/14566; A61M 5/31565; A61M 2005/14252; A61M 2005/14506; A61M 2005/14573; A61M 2005/31518; A61M 5/2455; A61M 5/3287; A61M 2005/14268; A61M 2005/1426; A61M 2005/3231; A61M 5/322; A61M 5/3221
   See application file for complete search history.

(56) References Cited

U.S. PATENT DOCUMENTS

| | | |
|---|---|---|
| 2,752,918 A | 7/1956 | Uytenbogaart et al. |
| 3,176,712 A | 4/1965 | Ramsden |
| 3,297,260 A | 1/1967 | Barlow |
| 3,464,359 A | 9/1969 | King |
| 3,885,662 A | 5/1975 | Schaefer |
| 3,946,732 A | 3/1976 | Hurscham |
| 3,947,692 A | 3/1976 | Payne |
| 3,993,061 A | 11/1976 | OLeary |
| 4,108,177 A | 8/1978 | Pistor |
| 4,152,098 A | 5/1979 | Moody et al. |
| 4,210,173 A | 7/1980 | Choksi et al. |
| 4,221,219 A | 9/1980 | Tucker |
| 4,257,324 A | 3/1981 | Stefansson et al. |
| 4,268,150 A | 5/1981 | Chen |
| 4,277,226 A | 7/1981 | Archibald |
| 4,313,439 A | 2/1982 | Babb et al. |
| 4,371,790 A | 2/1983 | Manning et al. |
| 4,417,889 A | 11/1983 | Choi |
| 4,424,720 A | 1/1984 | Bucchianeri |
| 4,435,173 A | 3/1984 | Siposs et al. |
| 4,475,905 A | 10/1984 | Himmelstrup |
| 4,498,843 A | 2/1985 | Schneider et al. |
| 4,507,115 A | 3/1985 | Kambara et al. |
| 4,551,134 A | 11/1985 | Slavik et al. |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,755,169 A | 7/1988 | Sarnoff et al. |
| 4,766,889 A | 8/1988 | Trick et al. |
| 4,808,161 A | 2/1989 | Kamen |
| 4,846,797 A | 7/1989 | Howson et al. |
| 4,858,619 A | 8/1989 | Toth |
| 4,898,579 A | 2/1990 | Groshong et al. |
| 4,908,017 A | 3/1990 | Howson et al. |
| 4,908,022 A * | 3/1990 | Haber ................ A61M 5/3129 604/110 |
| 4,944,659 A | 7/1990 | Labbe et al. |
| 4,969,874 A | 11/1990 | Michel et al. |
| 4,991,743 A | 2/1991 | Walker |
| 5,007,458 A | 4/1991 | Marcus et al. |
| 5,020,325 A | 6/1991 | Henault |
| 5,062,841 A | 11/1991 | Siegel |
| 5,147,311 A | 9/1992 | Pickhard |
| 5,178,609 A | 1/1993 | Ishikawa |
| 5,205,819 A | 4/1993 | Ross et al. |
| 5,213,483 A | 5/1993 | Flaherty et al. |
| 5,222,362 A | 6/1993 | Maus et al. |
| 5,236,416 A | 8/1993 | McDaniel et al. |
| 5,261,882 A | 11/1993 | Sealfon |
| 5,261,884 A | 11/1993 | Stern et al. |
| 5,277,338 A | 1/1994 | Divall |
| 5,281,202 A | 1/1994 | Weber et al. |
| 5,346,476 A | 9/1994 | Elson |
| 5,364,342 A | 11/1994 | Beuchat et al. |
| 5,388,615 A | 2/1995 | Edlund et al. |
| 5,433,710 A | 7/1995 | VanAntwerp et al. |
| 5,503,628 A | 4/1996 | Fetters et al. |
| 5,520,661 A | 5/1996 | Lal et al. |
| 5,533,389 A | 7/1996 | Kamen et al. |
| 5,582,593 A | 12/1996 | Hultman |
| 5,618,269 A | 4/1997 | Jacobsen et al. |
| 5,628,309 A | 5/1997 | Brown |
| 5,637,095 A | 6/1997 | Nason et al. |
| 5,665,070 A | 9/1997 | McPhee |
| 5,713,875 A | 2/1998 | Tanner, II |
| 5,747,350 A | 5/1998 | Sattler |
| 5,748,827 A | 5/1998 | Holl et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,807,075 A | 9/1998 | Jacobsen et al. |
| 5,839,467 A | 11/1998 | Saaski et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,957,890 A | 9/1999 | Mann et al. |
| 5,961,492 A | 10/1999 | Kriesel et al. |
| 5,971,963 A | 10/1999 | Choi |
| 6,019,747 A | 2/2000 | McPhee |
| 6,050,457 A | 4/2000 | Arnold et al. |
| 6,068,615 A | 5/2000 | Brown et al. |
| 6,086,615 A | 7/2000 | Wood et al. |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,352,522 B1 | 3/2002 | Kim et al. |
| 6,363,609 B1 | 4/2002 | Pickren |
| 6,375,638 B2 | 4/2002 | Nason et al. |
| 6,474,219 B2 | 11/2002 | Klitmose et al. |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesel et al. |
| 6,539,286 B1 | 3/2003 | Jiang |
| 6,569,115 B1 | 5/2003 | Barker et al. |
| 6,595,956 B1 | 7/2003 | Gross et al. |
| 6,656,158 B2 | 12/2003 | Mahoney et al. |
| 6,699,218 B2 | 3/2004 | Flaherty et al. |
| 6,723,072 B2 | 4/2004 | Flaherty et al. |
| 6,749,407 B2 | 6/2004 | Xie et al. |
| 6,851,260 B2 | 2/2005 | Mernoe |
| 6,883,778 B1 | 4/2005 | Newton et al. |
| 7,018,360 B2 | 3/2006 | Flaherty et al. |
| 7,104,275 B2 | 9/2006 | Dille |
| 7,128,727 B2 | 10/2006 | Flaherty et al. |
| 7,144,384 B2 | 12/2006 | Gorman et al. |
| 7,160,272 B1 | 1/2007 | Eyal et al. |
| 7,410,478 B2 * | 8/2008 | Yang ................ A61M 5/3234 604/110 |
| 7,771,392 B2 | 8/2010 | De Polo et al. |
| 7,914,499 B2 | 3/2011 | Gonnelli et al. |
| 7,951,114 B2 | 5/2011 | Rush et al. |
| 8,267,921 B2 | 9/2012 | Yodfat et al. |
| 8,382,703 B1 | 2/2013 | Abdelaal |
| 8,499,913 B2 | 8/2013 | Gunter |

(56) References Cited

U.S. PATENT DOCUMENTS

| | | | |
|---|---|---|---|
| 8,905,995 B2 * | 12/2014 | Mernoe | A61M 5/14566 604/500 |
| 8,920,376 B2 | 12/2014 | Caffey et al. | |
| 8,939,935 B2 | 1/2015 | O'Connor et al. | |
| 9,180,244 B2 | 11/2015 | Anderson et al. | |
| 9,192,716 B2 | 11/2015 | Jugl et al. | |
| 9,402,950 B2 | 8/2016 | Dilanni et al. | |
| 9,539,596 B2 | 1/2017 | Ikushima | |
| 10,441,723 B2 | 10/2019 | Nazzaro | |
| 10,695,485 B2 | 6/2020 | Nazzaro | |
| 2001/0016710 A1 | 8/2001 | Nason et al. | |
| 2001/0056258 A1 | 12/2001 | Evans | |
| 2002/0029018 A1 | 3/2002 | Jeffrey | |
| 2002/0032374 A1 | 3/2002 | Holker et al. | |
| 2002/0037221 A1 | 3/2002 | Mastrangelo et al. | |
| 2002/0173769 A1 | 11/2002 | Gray et al. | |
| 2002/0173830 A1 | 11/2002 | Starkweather et al. | |
| 2003/0040715 A1 | 2/2003 | D'Antonio et al. | |
| 2003/0055380 A1 | 3/2003 | Flaherty | |
| 2003/0097092 A1 | 5/2003 | Flaherty | |
| 2003/0109827 A1 | 6/2003 | Lavi et al. | |
| 2003/0163097 A1 | 8/2003 | Fleury et al. | |
| 2003/0198558 A1 | 10/2003 | Nason et al. | |
| 2003/0199825 A1 | 10/2003 | Flaherty | |
| 2004/0010207 A1 | 1/2004 | Flaherty et al. | |
| 2004/0064088 A1 | 4/2004 | Gorman et al. | |
| 2004/0068224 A1 | 4/2004 | Couvillon et al. | |
| 2004/0069044 A1 | 4/2004 | Lavi et al. | |
| 2004/0092865 A1 | 5/2004 | Flaherty et al. | |
| 2004/0094733 A1 | 5/2004 | Hower et al. | |
| 2004/0153032 A1 | 8/2004 | Garribotto et al. | |
| 2005/0020980 A1 | 1/2005 | Inoue et al. | |
| 2005/0165363 A1 | 7/2005 | Judson et al. | |
| 2005/0203461 A1 | 9/2005 | Flaherty et al. | |
| 2005/0238507 A1 | 10/2005 | Dilanni et al. | |
| 2005/0273059 A1 | 12/2005 | Mernoe et al. | |
| 2005/0277882 A1 | 12/2005 | Kriesel | |
| 2006/0041229 A1 | 2/2006 | Garibotto et al. | |
| 2006/0079765 A1 | 4/2006 | Neer et al. | |
| 2006/0155210 A1 | 7/2006 | Beckman et al. | |
| 2006/0173439 A1 | 8/2006 | Thorne et al. | |
| 2006/0178633 A1 | 8/2006 | Garibotto et al. | |
| 2006/0253085 A1 | 11/2006 | Geismar et al. | |
| 2006/0282290 A1 | 12/2006 | Flaherty et al. | |
| 2007/0005018 A1 | 1/2007 | Tekbuchava | |
| 2007/0073236 A1 * | 3/2007 | Mernoe | A61M 5/14244 604/151 |
| 2007/0088271 A1 | 4/2007 | Richards | |
| 2007/0118405 A1 | 5/2007 | Campbell et al. | |
| 2007/0282269 A1 | 12/2007 | Carter et al. | |
| 2008/0004515 A1 | 1/2008 | Jennewine | |
| 2008/0051738 A1 | 2/2008 | Griffin | |
| 2008/0114304 A1 | 5/2008 | Nalesso et al. | |
| 2008/0172028 A1 | 7/2008 | Blomquist | |
| 2008/0243211 A1 | 10/2008 | Cartwright et al. | |
| 2008/0294040 A1 | 11/2008 | Mohiuddin et al. | |
| 2009/0024083 A1 | 1/2009 | Kriesel et al. | |
| 2009/0062767 A1 | 3/2009 | Van Antwerp et al. | |
| 2009/0198215 A1 | 8/2009 | Chong et al. | |
| 2009/0278875 A1 | 11/2009 | Holm et al. | |
| 2009/0326472 A1 | 12/2009 | Carter et al. | |
| 2010/0036326 A1 | 2/2010 | Matusch | |
| 2010/0152658 A1 | 6/2010 | Hanson et al. | |
| 2010/0241066 A1 | 9/2010 | Hansen et al. | |
| 2011/0054399 A1 | 3/2011 | Chong et al. | |
| 2011/0073620 A1 | 3/2011 | Verrilli | |
| 2011/0144586 A1 | 6/2011 | Michaud et al. | |
| 2011/0180480 A1 | 7/2011 | Kloeffel et al. | |
| 2011/0230833 A1 | 9/2011 | Landman et al. | |
| 2012/0078161 A1 | 3/2012 | Masterson et al. | |
| 2012/0172817 A1 * | 7/2012 | Bruggemann | A61M 5/14566 604/218 |
| 2012/0209207 A1 | 8/2012 | Gray et al. | |
| 2013/0006213 A1 | 1/2013 | Arnitz et al. | |
| 2013/0017099 A1 | 1/2013 | Genoud et al. | |
| 2013/0064701 A1 | 3/2013 | Konishi | |
| 2013/0177455 A1 | 7/2013 | Kamen et al. | |
| 2013/0178803 A1 | 7/2013 | Raab | |
| 2013/0245545 A1 | 9/2013 | Arnold et al. | |
| 2013/0267932 A1 | 10/2013 | Franke et al. | |
| 2013/0296792 A1 | 11/2013 | Cabiri | |
| 2014/0018730 A1 | 1/2014 | Muller-Pathle | |
| 2014/0127048 A1 | 5/2014 | Dilanni et al. | |
| 2014/0128839 A1 | 5/2014 | Dilanni et al. | |
| 2014/0142508 A1 | 5/2014 | Dilanni et al. | |
| 2014/0148784 A1 | 5/2014 | Anderson et al. | |
| 2014/0171901 A1 | 6/2014 | Langsdorf et al. | |
| 2015/0041498 A1 | 2/2015 | Kakiuchi et al. | |
| 2015/0051487 A1 | 2/2015 | Uber et al. | |
| 2015/0057613 A1 | 2/2015 | Clemente et al. | |
| 2015/0064036 A1 | 3/2015 | Eberhard | |
| 2015/0137017 A1 | 5/2015 | Ambrosina et al. | |
| 2015/0202386 A1 | 7/2015 | Brady et al. | |
| 2015/0290389 A1 | 10/2015 | Nessel | |
| 2015/0297825 A1 | 10/2015 | Focht et al. | |
| 2016/0008549 A1 | 1/2016 | Plumptre et al. | |
| 2016/0025544 A1 | 1/2016 | Kamen et al. | |
| 2016/0055842 A1 | 2/2016 | DeFranks et al. | |
| 2016/0082242 A1 | 3/2016 | Burton et al. | |
| 2016/0129190 A1 | 5/2016 | Haitsuka | |
| 2016/0193423 A1 | 7/2016 | Bilton | |
| 2016/0213851 A1 | 7/2016 | Weibel et al. | |
| 2017/0021096 A1 | 1/2017 | Cole et al. | |
| 2017/0021137 A1 | 1/2017 | Cole | |
| 2017/0100541 A1 | 4/2017 | Constantineau et al. | |
| 2017/0216516 A1 | 8/2017 | Dale et al. | |
| 2017/0239415 A1 | 8/2017 | Hwang et al. | |
| 2017/0290975 A1 | 10/2017 | Barmaimon et al. | |
| 2018/0021521 A1 | 1/2018 | Sanchez | |
| 2018/0185579 A1 | 7/2018 | Joseph et al. | |
| 2018/0313346 A1 | 11/2018 | Oakes et al. | |
| 2019/0192782 A1 | 6/2019 | Pedersen et al. | |
| 2019/0365993 A1 | 12/2019 | Staub et al. | |
| 2020/0009315 A1 | 1/2020 | Brouet et al. | |
| 2020/0345931 A1 | 11/2020 | Gray et al. | |

FOREIGN PATENT DOCUMENTS

| | | |
|---|---|---|
| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 4200595 A1 | 7/1993 |
| DE | 19723648 C1 | 8/1998 |
| DE | 102005040344 A1 | 3/2007 |
| EP | 0454331 A1 | 10/1991 |
| EP | 0789146 A1 | 8/1997 |
| EP | 0867196 A2 | 9/1998 |
| EP | 1065378 A2 | 1/2001 |
| EP | 1177802 A1 | 2/2002 |
| EP | 1403519 A1 | 3/2004 |
| EP | 2397181 A1 | 12/2011 |
| EP | 2468338 A1 | 6/2012 |
| EP | 2703024 A1 | 3/2014 |
| EP | 1874390 B1 | 10/2014 |
| EP | 2830499 A1 | 2/2015 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 357139 A | 9/1931 |
| GB | 810488 A | 3/1959 |
| GB | 875034 A | 8/1961 |
| GB | 1204836 A | 9/1970 |
| GB | 2008806 A | 6/1979 |
| GB | 2077367 A | 12/1981 |
| GB | 2456681 A | 7/2009 |
| GB | 2549750 A | 11/2017 |
| IL | 46017 A | 11/1977 |
| JP | 06063133 A | 3/1994 |
| JP | H06296690 A | 10/1994 |
| JP | H08238324 A | 9/1996 |

(56) References Cited

FOREIGN PATENT DOCUMENTS

| | | | |
|---|---|---|---|
| JP | 2004247271 A | 9/2004 | |
| JP | 2004274719 A | 9/2004 | |
| JP | 2005188355 A | 7/2005 | |
| JP | 2006159228 A | 6/2006 | |
| JP | 2006249130 A | 9/2006 | |
| JP | 2009514580 A | 4/2009 | |
| JP | 6098988 B2 | 4/2014 | |
| JP | 2017513577 A | 6/2017 | |
| NL | 1019126 C1 | 4/2003 | |
| WO | 8101658 A1 | 6/1981 | |
| WO | 8606796 A1 | 11/1986 | |
| WO | 9320864 A1 | 10/1993 | |
| WO | 9415660 A1 | 7/1994 | |
| WO | 9855073 A1 | 12/1998 | |
| WO | 9856293 A1 | 12/1998 | |
| WO | 9910040 A1 | 3/1999 | |
| WO | 9910049 A1 | 3/1999 | |
| WO | 9962576 A1 | 12/1999 | |
| WO | 0029047 A1 | 5/2000 | |
| WO | 0178812 A1 | 10/2001 | |
| WO | 0220073 A2 | 3/2002 | |
| WO | 2002026282 A2 | 4/2002 | |
| WO | 02068823 A1 | 9/2002 | |
| WO | 2002076535 A1 | 10/2002 | |
| WO | 2003097133 A1 | 11/2003 | |
| WO | 2004032994 A2 | 4/2004 | |
| WO | 2004056412 A2 | 7/2004 | |
| WO | 2004110526 A1 | 12/2004 | |
| WO | 2007066152 A2 | 6/2007 | |
| WO | 2008133702 A1 | 11/2008 | |
| WO | 2009039203 A2 | 3/2009 | |
| WO | 2009141005 A1 | 11/2009 | |
| WO | 2010022069 A2 | 2/2010 | |
| WO | 2010077279 A1 | 7/2010 | |
| WO | 2010139793 A1 | 12/2010 | |
| WO | 2011010198 A2 | 1/2011 | |
| WO | 2011031458 A1 | 3/2011 | |
| WO | 2011069935 A2 | 6/2011 | |
| WO | 2011075042 A1 | 6/2011 | |
| WO | 2011133823 A1 | 10/2011 | |
| WO | 2012073032 A1 | 6/2012 | |
| WO | 2013050535 A2 | 4/2013 | |
| WO | 2013137893 A1 | 9/2013 | |
| WO | 2013149186 A1 | 10/2013 | |
| WO | 2014029416 A1 | 2/2014 | |
| WO | 2014149357 A1 | 9/2014 | |
| WO | 2014179774 A1 | 11/2014 | |
| WO | 2015032772 A1 | 3/2015 | |
| WO | 2015048791 A1 | 4/2015 | |
| WO | 2015081337 A2 | 6/2015 | |
| WO | 2015117854 A1 | 8/2015 | |
| WO | 2015167201 A1 | 11/2015 | |
| WO | 2015177082 A1 | 11/2015 | |
| WO | WO-2017089253 A1 * | 6/2017 | ........ A61M 5/31511 |
| WO | 2017148855 A1 | 9/2017 | |
| WO | 2017187177 A1 | 11/2017 | |
| WO | 2021016452 A1 | 1/2021 | |

OTHER PUBLICATIONS

Author unknown, "The Animas R-1000 Insulin Pump—Animas Corporation intends to exit the insulin pump business and discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/, 2 pages.

Author unknown, CeramTec "Discover the Electro Ceramic Products CeramTec acquired from Morgan Advanced Materials" [online], Mar. 1, 2001 [retrieved on Jan. 8, 2019. Retrieved from the Internet URL: http://www.morgantechnicalceramics.com/, 2 pages.

Vaughan, M.E., "The Design, Fabrication, and Modeling of a Piezoelectric Linear Motor." Master's thesis, Virginia Polytechnic Institute and State University, VA. (2001), 93 pages.

Galante, et al., "Design, Modeling, and Performance of a High Force Piezoelectric Inchworm Motor," Journal of Intelligent Material Systems and Structures, vol. 10, 962-972 (1999), 11 pages.

International Search Report and Written Opinion for International Application No. PCT/US2018/014351, dated Jun. 4, 2018, 9 pages.

International Search Report and Written Opinion for International Application No. PCT/US2017/055054, dated Jan. 25, 2018, 13 pages.

International Search Report and Written Opinion for International Application No. PCT/US2018/045155, dated Oct. 15, 2018, 15 pages.

International Search Report and Written Opinion for International Application No. PCT/US2017/034811, dated Oct. 18, 2017, 17 pages.

International Search Report and Written Opinion for International Application No. PCT/US2017/046508, dated Jan. 17, 2018, 14 pages.

International Search Report and Written Opinion for International Application No. PCT/US2017/034814, dated Oct. 11, 2017, 18 pages.

International Search Report and Written Opinion for International Application No. PCT/US2017/046777, dated Dec. 13, 2017, 14 pages.

International Search Report and Written Opinion for International Application No. PCT/US2017/046737, dated Dec. 14, 2017, 11 pages.

International Search Report and Written Opinion for Application No. PCT/US2019/059854, dated Aug. 26, 2020, 15 pages.

European Search Report and Written Opinion for the European Patent Application No. EP20174878, dated Sep. 29, 2020, 8 pages.

European Search Report and Written Opinion for the European Patent Application No. EP19177571, dated Oct. 30, 2019, 8 pages.

International Search Report and Written Opinion for the International Patent Application No. PCT/US2019/035756, dated Jul. 31, 2019, 11 pages.

International Preliminary Report on Patentability for the International Patent Application No. PCT/US18/14351, dated Aug. 1, 2019, 7 pages.

International Preliminary Report on Patentability for the International Patent Application No. PCT/US2017/046777, dated Feb. 19, 2019, 8 pages.

International Preliminary Report on Patentability for the International Patent Application No. PCT/US2017/046737, dated Feb. 19, 2019, 8 pages.

International Preliminary Report on Patentability for the International Patent Application No. PCT/US2017/055054, dated Apr. 9, 2019, 8 pages.

EPO Search Report dated Nov. 11, 2015, received in corresponding Application No. 13768938.6, 7 pages.

PCT International Search Report and Written Opinion dated Aug. 6, 2013, received in corresponding PCT Application No. PCT/US13/34674, pp. 1-19.

International Search Report and Written Opinion for International application No. PCT/GB2007/004073, dated Jan. 31, 2008, 8 pages.

International Search Report and Written Opinion for the International Patent Application No. PCT/US2019/063615, dated May 3, 2020, 16 pages.

International Preliminary Report on Patentability for the International Patent Application No. PCT/US2018/045155, dated Feb. 13, 2020, 10 pages.

International Preliminary Report on Patentability for the International Patent Application No. PCT/US2017/046508 dated Feb. 12, 2019, 10 pages.

International Preliminary Report on Patentability for the International Patent Application No. PCT/US2017/034811, dated Nov. 27, 2018, 10 pages.

International Search Report and Written Opinion for the International Patent Application No. PCT/US2021/055581, dated Feb. 8, 2022, 19 pages.

International Search Report and Written Opinion for the International Patent Application No. PCT/US2022/011356, dated Apr. 29, 2022, 19 pages.

(56) References Cited

OTHER PUBLICATIONS

International Search Report and Written Opinion, Application No. PCT/US2022/016713, dated Aug. 5, 2022, 19 pages.
International Search Report and Written Opinion for International Patent Application No. PCT/US2022/029012, dated Aug. 19, 2022, 12 pages.

* cited by examiner

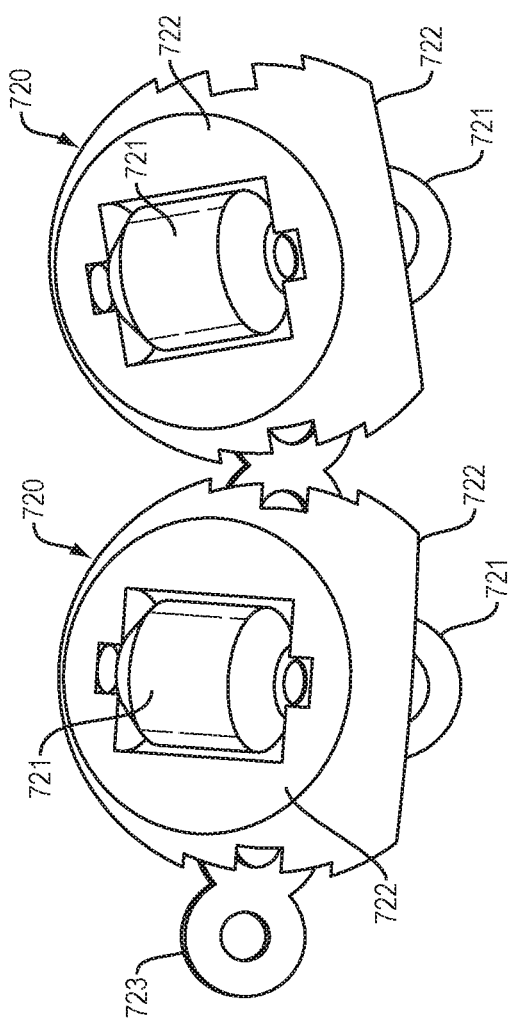
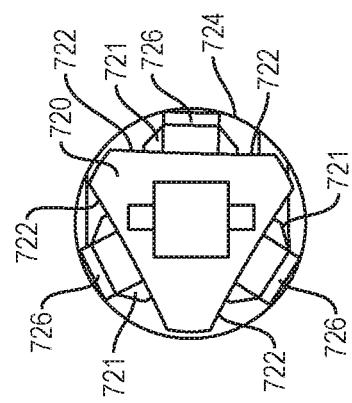
FIG. 7A
FIG. 7B

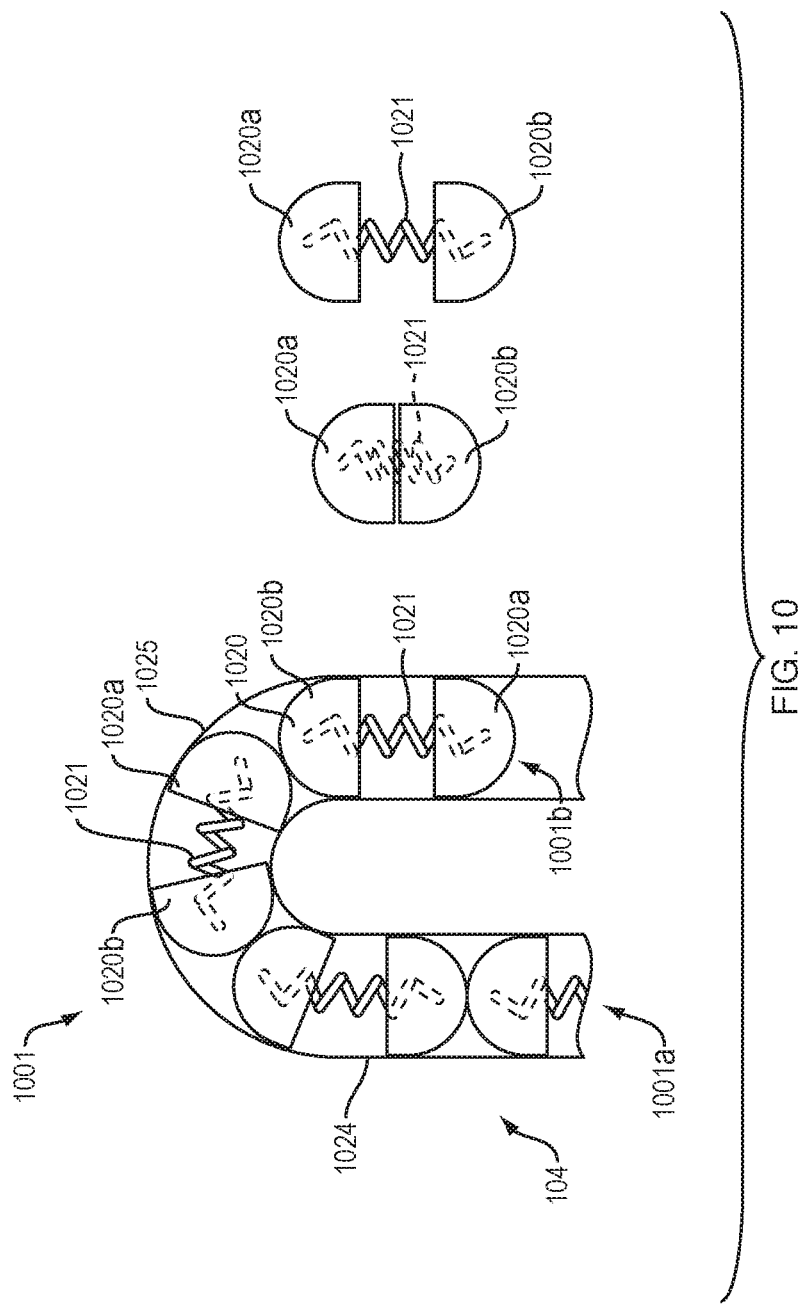

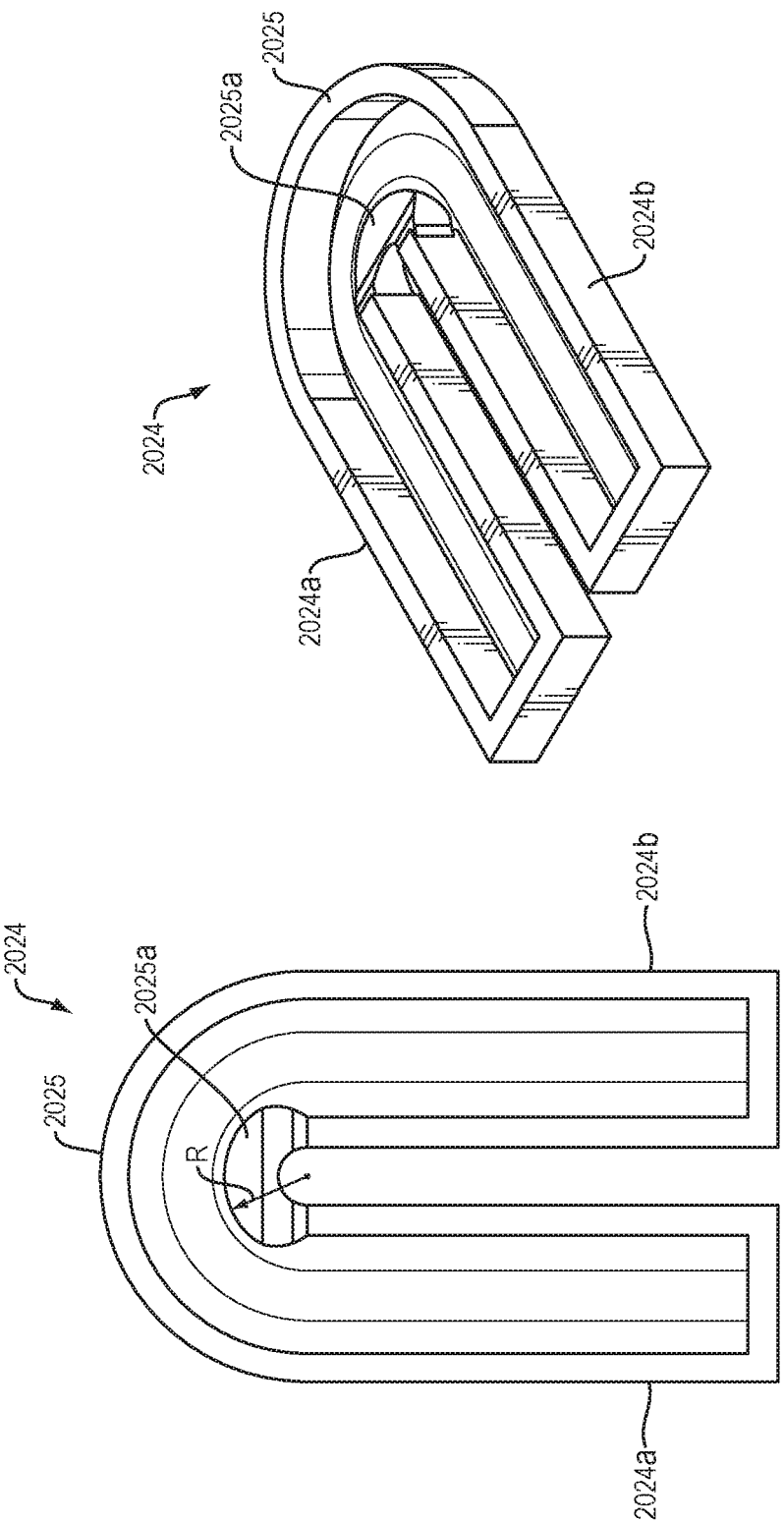

DRUG DELIVERY DEVICES, SYSTEMS, AND METHODS WITH FORCE TRANSFER ELEMENTS

PRIORITY

This application claims the benefit of priority under 35 USC § 119 to U.S. Provisional Application Ser. No. 62/562,802, filed Sep. 25, 2017, which is incorporated by reference in its entirety and for all purposes.

TECHNICAL FIELD

Embodiments generally relate to medication delivery. More particularly, embodiments relate to force transfer elements used to actuate wearable drug delivery devices.

BACKGROUND

Many conventional drug delivery systems, such as hand-held auto-injectors, are designed to rapidly delivery a drug to a patient. These conventional drug delivery systems are generally not suitable for delivering a drug to a user over relatively longer periods of time as may be required for many drugs.

As an alternative to conventional auto-injectors, many conventional drug delivery systems are designed to be wearable and to deliver a drug more slowly to the patient. However, these conventional wearable drug delivery systems often require a patient to transfer a drug or other medicine from a vial to a container within the drug delivery system. Transferring the drug can be a challenging task for many patients as it may require precise handling of the drug, a transfer mechanism (e.g., a syringe), and the drug delivery system. Some conventional wearable drug delivery systems use prefilled cartridges that contain the drug intended for the patient, obviating the need for such drug transfers. However, these conventional cartridge-based drug delivery systems are often bulky and cumbersome due to the included cartridge and can be uncomfortable when worn by the patient.

A need therefore exists for a more convenient and user-friendly wearable drug delivery device for providing a drug to a user.

SUMMARY

The present invention in various embodiments includes drug delivery devices, systems, and methods with force transfer elements. Fluids may be driving through and/or out of devices with force transfer elements and/or drive mechanisms of this disclosure.

In one aspect of the present invention, a drug delivery device may include a drug container for storing a liquid drug. A first end of the drug container may be sealed by a plunger. A needle conduit may be coupled to the plunger. A needle insertion component may be coupled to the needle conduit. A drive mechanism may be coupled to the plunger. The drive mechanism may include a drive spring and a plurality of linked force transfer elements. The plurality of linked force transfer elements may include a plurality of spherical body links. The spherical body may link each comprise partial spherical sections that may be coupled to adjacent body links via a ball and recess connection. The spherical body links may each include spherical sections coupled to connector links via a disc and recess connection. The linked force transfer elements may include partial spherical sections that may each having at least one roller coupled thereto. The plurality of linked force transfer element may include a plurality of chain links. Each of the plurality of chain links may include a depending portion that may be configured to be received in a recess portion of an adjacent chain link to enable adjacent links to pivot with respect to each other.

In another aspect, a drug delivery device may include a drug container for storing a liquid drug. A first end of the drug container may be sealed by a plunger. A needle conduit may be coupled to the plunger. A needle insertion component may be coupled to the needle conduit. A drive mechanism may be coupled to the plunger. The drive mechanism may include a drive spring and may include a plurality of non-spherical force transfer elements. The plurality of non-spherical force transfer elements may include a plurality of dog bone shaped links. Each of the plurality of non-spherical force transfer elements may comprise first and second shells biased apart by an elastic element. Each of the plurality of non-spherical force transfer elements may comprise a flexible rod and first and second guide rollers. Each of the plurality of non-spherical force transfer elements may include first and second roller elements and may include a reduced diameter section disposed therebetween. A bushed connecting rod may be coupled between adjacent one of said non-spherical force transfer elements. The bushed connecting rod may be rotatably coupled to the reduced diameter section of the non-spherical force transfer elements.

In another aspect, a drug delivery device may include a drug container for storing a liquid drug. A first end of the drug container may be sealed by a plunger. A needle conduit may be coupled to the plunger. A needle insertion component may be coupled to the needle conduit. A drive mechanism may be coupled to the plunger. The drive mechanism may include a drive spring and may include a plurality of substantially cylindrical force transfer elements. Each of the plurality of cylindrical force transfer elements may include a cylindrical portion having a groove and a protrusion. The groove and protrusion may be configured to engage a corresponding protrusion and a corresponding groove of an adjacent one of the plurality of cylindrical force transfer elements. The groove and the protrusion may be disposed adjacent each other at an upper end of each of said plurality of cylindrical force transfer elements. The groove and protrusion may be configured to engage the corresponding protrusion and the corresponding groove of said adjacent one of said plurality of cylindrical force transfer elements. The plurality of cylindrical force transfer elements may include a rail-engaging groove in the cylindrical portion, and may include a track-engaging portion configured to engage a rail disposed on a sidewall of a track of said drug delivery device. A substantially U-shaped track may have a straight track portion with walls spaced apart from each other a first distance, and a curved track portion with walls spaced apart from each other a second distance that may be smaller than the first distance. Each of the plurality of substantially cylindrical force transfer elements may include an hourglass shape having upper and lower portions that may be coupled by a reduced diameter portion. Each of the upper and lower portions may include a cylindrical portion that tapers to the reduced diameter portion to form upper and lower angled transition portions. The upper and lower angled portions may be straight angled portions. The upper and lower angled portions may each comprise curved portions.

BRIEF DESCRIPTION OF THE DRAWINGS

FIGS. 7A and 7B illustrate an arrangement of force transfer elements for use with the drug delivery device of FIG. 1 in accordance with an embodiment of the present disclosure.

FIG. 10 illustrates an arrangement of force transfer elements for use with the drug delivery device of FIG. 1 in accordance with an embodiment of the present disclosure.

FIGS. 20A and 20B illustrate an arrangement of a guide system for use with the force transfer elements of FIGS. 19A-19C and the drug delivery device of FIG. 1 in accordance with an embodiment of the present disclosure.

DETAILED DESCRIPTION

Figure 1:
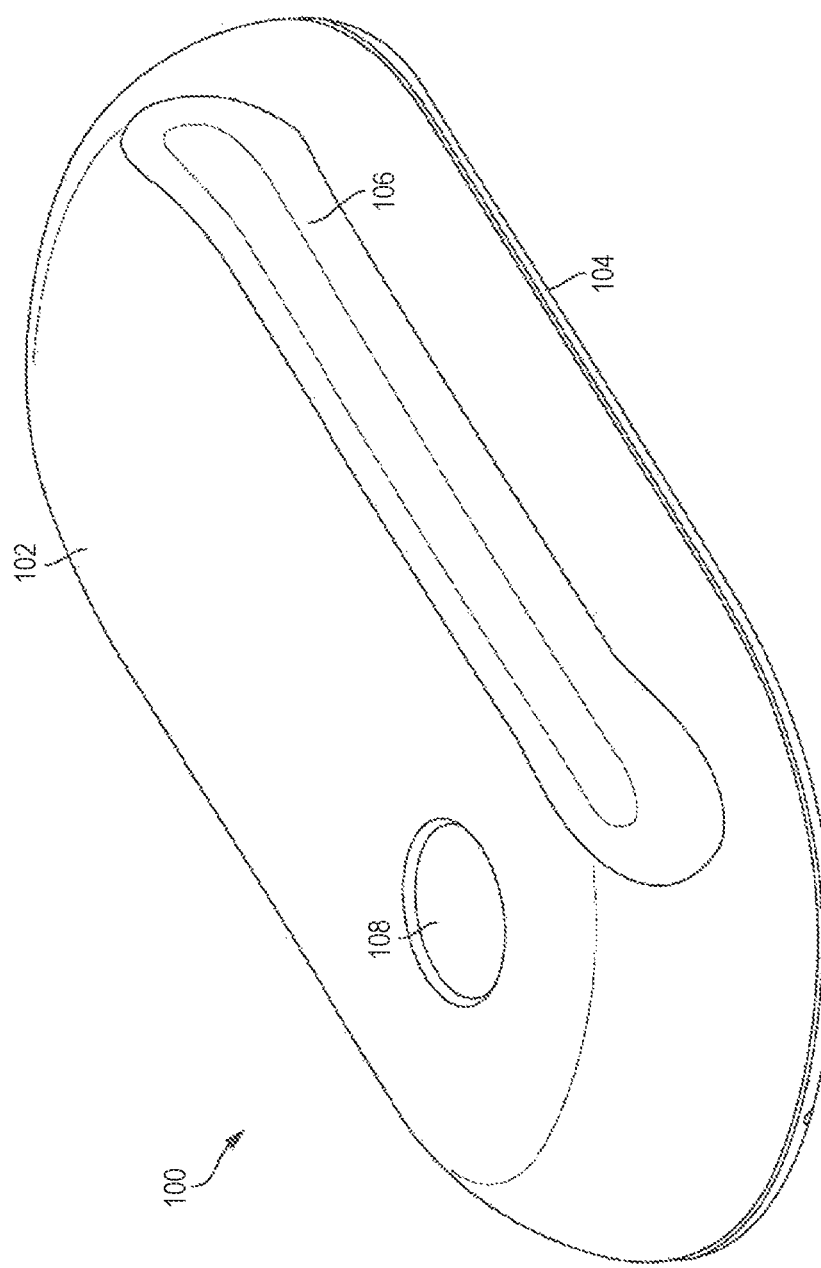
FIG. 1 illustrates an exemplary drug delivery device in accordance with an embodiment of the present disclosure.

The present disclosure is not limited to the particular embodiments described. The terminology used herein is for the purpose of describing particular embodiments only, and is not intended to be limiting. Unless otherwise defined, all technical terms used herein have the same meaning as commonly understood by one of ordinary skill in the art to which the disclosure belongs.

Although embodiments of the present disclosure are described with specific reference to drug delivery, including insulin, it should be appreciated that such systems, methods, and devices may be used in a variety of configurations of fluid delivery, with a variety of instruments, a variety of fluids, and for a variety of organs and/or cavities, such as the vascular system, urogenital system, lymphatic system, neurological system, and the like.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. The term "or" is generally employed in its sense including "and/or" unless the content clearly dictates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

This disclosure presents various systems, components, and methods for delivering a liquid drug or medicine to a patient or user. Each of the systems, components, and methods disclosed herein provides one or more advantages over conventional systems, components, and methods.

Various embodiments include a wearable drug delivery device that can deliver a liquid drug stored in a container to a patient or user. The container can be a prefilled cartridge that can be loaded into the drug delivery device by the patient or that can be preloaded within the drug delivery device when provided to the patient. A sealed end of the container can be pierced to couple the stored liquid drug to a needle conduit. The needle conduit can be coupled to a needle insertion component that provides access to the patient. A drive system of the drug delivery device can expel the liquid drug from the container to the patient through the needle conduit. The drive system can include an energy storage component and one or more energy/force transfer components to enable the drug delivery device to maintain a small form factor. The result is enhanced patient's comfort when using the drug delivery device. Other embodiments are disclosed and described.

FIG. 1 illustrates an embodiment of a drug delivery device 100 with force transfer elements according to the present disclosure. The drug delivery device 100 can include a top portion or cover 102 and a lower portion or base 104. The top portion 102 and the lower portion 104 can together form a housing of the drug delivery device 100. The top portion 102 and the lower portion 104 can be coupled together to form an outside of the drug delivery device 100. The top portion 102 and the lower portion 104 can be formed from any material including, for example, plastic, metal, rubber, or any combination thereof.

The drug delivery device 100 can be used to deliver a therapeutic agent (e.g., a drug) drug to a patient or user. In various embodiments, the drug delivery device 100 can include a container for retaining a liquid drug. The drug delivery device 100 can be used to deliver the liquid drug from the container to the patient. Any type of liquid drug can be stored by the drug delivery device 100 and delivered to a patient. In various embodiments, the container can contain any therapeutic agent such as, for example, a drug, a subcutaneous injectable, a medicine, or a biologic. A patient receiving a drug or other medicine (or any liquid) from the drug delivery device 100 can also be referred to as a user.

The drug delivery device 100 can operate as a bolus drug delivery device. In general, the drug delivery device 100 can provide any amount of the stored liquid drug to a patient over any period of time. In various embodiments, the drug delivery device 100 can provide the stored liquid drug to the patient in a single dose over a desired amount of time. In various embodiments, the drug delivery device 100 can provide the stored liquid drug to the patient over multiple doses.

As shown in FIG. 1, the top portion 102 of the drug delivery device 100 can include a raised portion 106. The raised portion 106 can be elongated and run along a side of the drug delivery device 100. A liquid drug cartridge can be approximately positioned under the raised portion 106 such that the raised portion 106 accommodates the size and positioning of the liquid drug container within the drug delivery device 102. The top portion 102 can also include a patient interaction element or component 108. In various embodiments, the patient interaction element 108 can be a push button or other patient input device. The patient interaction element 108 can be used to activate the drug delivery device 100.

The drug delivery device 100 can be a wearable drug delivery device 100. As a wearable device, the drug delivery device 100 can be an on-body delivery system (OBDS). The drug delivery device 100 can be coupled to a patient in a number of ways. For example, the lower portion 104 of the drug delivery device 100 can include an adhesive for attaching to a patient. In various embodiments, the drug delivery device 100 can be attached to a secondary device attached or worn by the patient such that the drug delivery device 100 fits onto or can be coupled to the secondary device.

Figure 2:
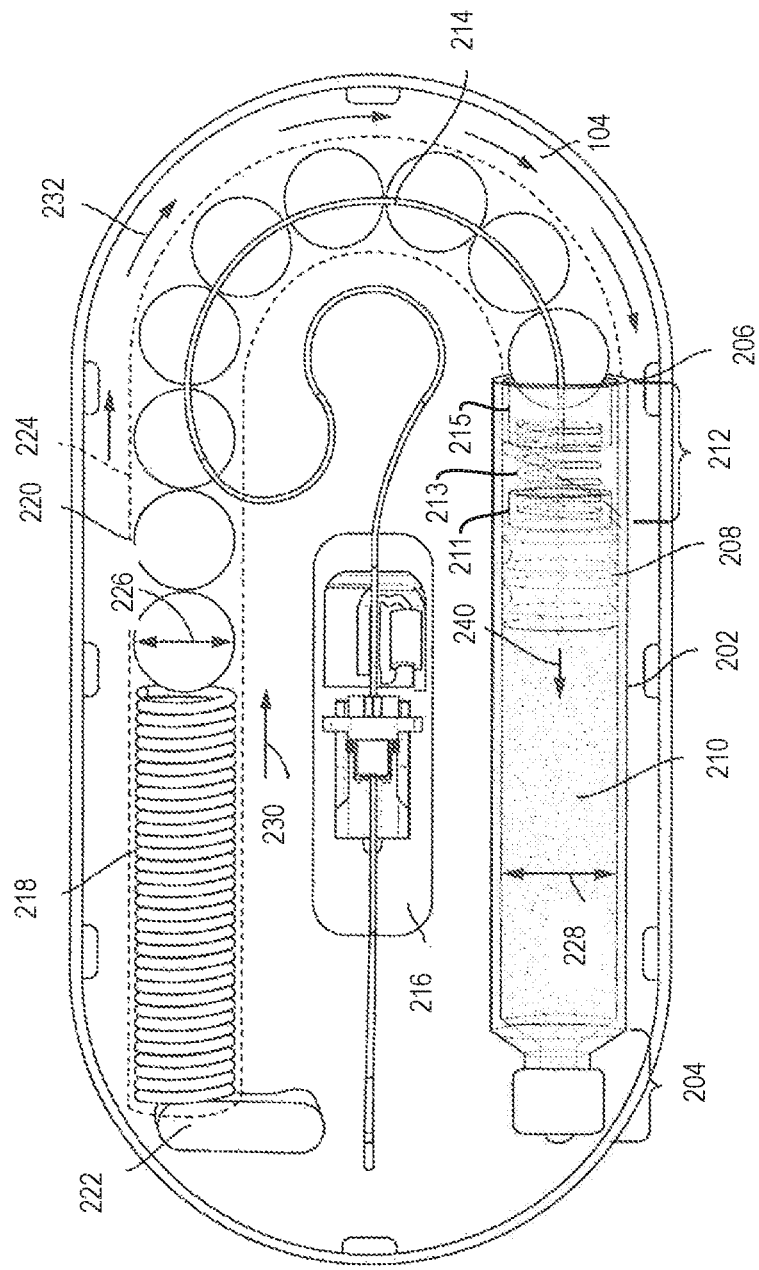
FIG. 2 illustrates an arrangement of internal components of the drug delivery devices of FIG. 1 in accordance with an embodiment of the present disclosure.

FIG. 2 illustrates an arrangement of internal components of the drug delivery device 100 with force transfer elements according to the present disclosure. For example, FIG. 2 shows various internal components of the drug delivery device 100 when the top portion 102 of the drug delivery device 100 is removed. The drug delivery device 100 can include a drug container 202. The drug container 202 can include a first end 204 and a second end 206. The drug container 202 can be sealed at or near the first end 204 and the second end 206. The first end 204 can include a neck and a cap as shown. The second end 206 can include a plunger 208. A liquid drug 210 can be contained between a sealing arrangement provided at the first end 204 of the drug container 202 and the plunger 208. As an example, the first end 204 of the drug container 202 can be sealed by a septum. The drug container 202 of the drug delivery device 100 can be a drug cartridge such as, for example, an ISO standardized drug cartridge.

The liquid drug 210 is accessed through the second end 206 of the drug container 202. A drug container access mechanism or component 212 can be positioned at or near the second end 206 for accessing the liquid drug 210. As shown, the drug container access mechanism 212 can access the liquid drug 210 through the plunger 208. The drug container access mechanism 212 can include a needle or other component at an end of the needle conduit 214 to pierce the plunger 208 to access the liquid drug 210. The access mechanism 212 can include an access spring 213 disposed between a first plate 211 and a second plate 215. The first and second plates 211, 215 can include a wall configured to contain the access spring 213. One or more force transfer elements (e.g., force transmitting spheres 220) can be at least partially disposed within and/or adjacent the second plate 215. The access spring 213 can provide a force load against the force transmitting spheres 220 to keep them substantially stable within the device. The needle and/or the needle conduit 214 can extend over (but not in contact with) one or more force transmitting spheres 220, bend at about 90° through the second plate 215 (e.g., through a wall of the second plate 215), bend at about 90° such that the needle conduit extends substantially parallel through a central axis of the access spring 213, through a central aperture of the first plate 211, and at least partially through an end of the plunger 208. Prior to piercing through a second end of the plunger 208, the plunger 208 may have one or both ends remain unpierced and the liquid drug 210 inaccessible and sealed within the drug container 202. The drug container access mechanism 212 can remain in an idle state prior to being activated to access the liquid drug 210. After activation, the needle of the drug container access mechanism 212 can extend through the plunger 208.

The drug container access mechanism 212 can couple the liquid drug 210 to a needle conduit 214. The needle conduit 214 can include tubing (e.g., plastic tubing or metal tubing) and can provide a path for a portion of the liquid drug 210 that is expelled from the primary drug container 202. The needle conduit 214 can route the liquid drug 210 from the primary drug container 202 to a needle insertion mechanism or component 216. The needle insertion mechanism 216 can provide an entry point to a patient. The needle insertion mechanism 216 can include a hard needle and/or a soft needle or cannula that provides access to the patient such that the liquid drug 210 can be delivered to the patient.

As further shown in FIG. 2, the drug delivery device 100 can also include a drive spring 218 and a plurality of force transfer elements (e.g., force transmitting spheres 220), which in the illustrated embodiment are ball bearings. The force transmitting spheres 220 can be formed of any type of material including glass, metal (e.g., stainless steel), a polymer, other plastic, or the like.

The drive spring 218 and the force transmitting spheres 220 can be used to expel the liquid drug 210 from the primary drug container 202. In particular, the drive spring 218 can apply a force that can be applied to the spheres 220. The force transmitting spheres 220 can be arranged to transfer the force from the drive spring 218 to the plunger 208. When the force from the drive spring 218 is applied to the plunger 208, the plunger 208 can advance into the drug container 202 (toward the first end 204). As the plunger 208 advances into the drug container 202, the liquid drug 210 within the drug container 202 can be forced into the needle conduit 214 and on to the needle insertion mechanism 216 for delivery to the patient.

In the illustrated embodiment, the drive spring 218 is a coil spring, though it will be appreciated that it could be any appropriate type of spring, and may consist of multiple springs. A dead bolt 222 or other fixed element can be positioned at one end of the drive spring 218 to provide a stable reference for the drive spring 218 (e.g., a push off point). The dead bolt 222 can be coupled to the inner top surface of the lower portion 104.

The bottom portion 104 of the drug delivery device 100 can include a track 224 for guiding the force transmitting spheres 220 as they are pushed by the drive spring 218 toward the plunger 208. The track 224 can completely surround or cover the force transmitting spheres 220, and can form any shape and can be arranged to take on any shape to guide the force transmitting spheres 220 from the drive spring 218 to the drug container 202.

Prior to activation, the drive spring 218 can be in an idle state. While in an idle state, the drive spring 218 can be compressed (e.g., as shown in FIG. 2). When activated, the drive spring 218 can be allowed to expand. For example, after activation, the drive spring 218 can be allowed to expand in a direction away from the dead bolt 222. When initially activated, the drive spring 218 can apply a force against the force transmitting spheres 220 which, in turn, press the plunger 208 into the drug container access mechanism 212 to cause a needle coupled to the needle conduit 214 to pierce the plunger 208.

Once the plunger 208 is pierced, the primary drug container 202 can be drained of its contents and delivered to a patient. The drive spring 218 and the force transmitting spheres 220 can be sized and adjusted to help regulate a flow of the liquid drug 210 from the primary drug container 202 to the needle insertion mechanism 216 based on a variety factors including the viscosity of the liquid drug 210 and the diameter of the needle conduit 214.

As shown in FIG. 2, when the drive spring 218 is allowed to expand it applies a force in a direction 230 against the force transmitting spheres 220. The direction 230 can correspond to a direction in which the drive spring 218 is allowed to expand, based on a positioning of the dead bolt 222, which can provide a thrust point for the drive spring 218. The force transmitting spheres 220 can translate or transfer the force from the drive spring 218 to the plunger 208. The force transmitting spheres 220 allow the force to be translated to a different direction than the original direction of the force. Specifically, the force transmitting spheres 220 can apply the force along a curved path, and finally in a direction toward the first end 204 of the primary drug container 202 relative to the second end 206 of the primary drug container 202. Consequently, the force transmitting spheres 220 enable the force provide by the drive spring 218 provided in a first direction to be applied to the plunger 208 in a second, approximately opposite direction, via, e.g., the second plate 215, access spring 213, and first plate 211, as described above.

As shown in FIG. 2, the direction 230 of the force provided by the drive spring 218 can cause the force transmitting spheres 220 to move in the direction 232—that is, through the track 224 toward the second end 206 of the primary drug container 202. The force transmitting spheres 220 can therefore transfer the force from the drive spring 218 to the plunger 208, thereby causing the plunger 208 to move in a direction 240. The movement of the plunger 208 in the direction 240 can force the liquid drug 210 out of the primary drug container 202 and into the needle conduit 214.

Although the embodiment of FIG. 2 includes a drug delivery device including a drive mechanism employing a plurality of force transmitting spheres 220, force may be transferred from the drive spring 218 to the plunger 208 using force transmitting elements having a variety of other configurations. Such alternative configurations are described throughout this disclosure. It will be appreciated that each of the described alternative force transmitting elements can be implemented in various drug delivery devices such as the drug delivery device 100 described in relation to FIGS. 1 and 2.

Figure 3B:
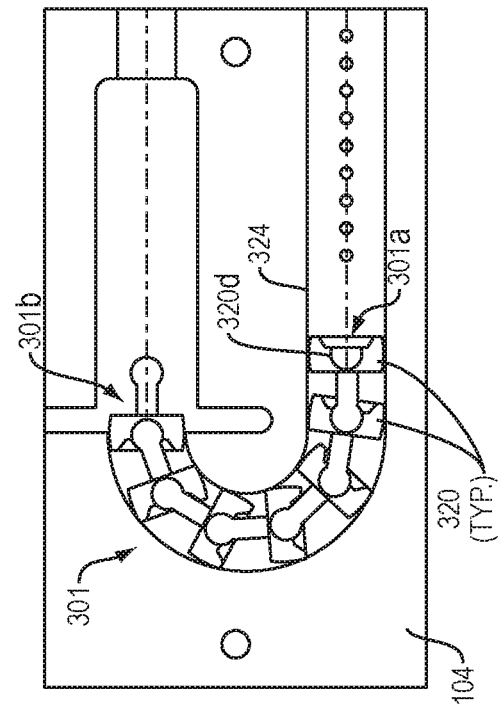
FIGS. 3A and 3B illustrate an arrangement of force transfer elements for use with the drug delivery device of FIG. 1 in accordance with an embodiment of the present disclosure.
Figure 3A:
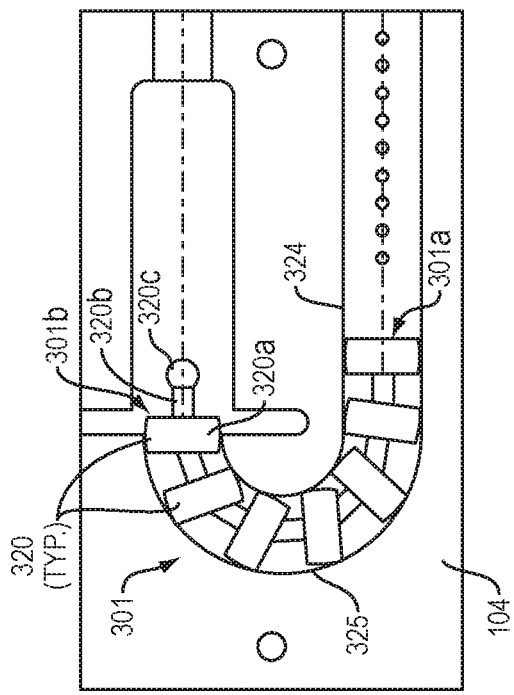

Referring to FIGS. 3A and 3B, a drive mechanism 301 with force transfer elements according to the present disclosure includes a plurality of spherical body links 320 disposed within a track 324 formed in or on the bottom 104 (FIG. 1) of the drug delivery device 100. Each spherical body link 320 includes a partial spherical portion 320a, a neck portion 320b, and a rounded head portion 320c. The partial spherical portions 320a each have a recess 320d therein for receiving the head portion 320c of an adjacent link. In some embodiments the recess 320d may receive the head portion 320c of an adjacent link via a snap-fit. The recess 320d is sized and shaped to enable the received head portion 320c to pivot therein, thus allowing the individual links to pivot with respect to each other. This, in turn, enables the drive mechanism 301 to move through the curved section 325 of the track 324. An advantage of this embodiment is that the spherical body links 320 can be shorter than a similarly sized sphere (e.g., 220), thus allowing for more individual links along the length of the drive mechanism 301. Such an arrangement can be a benefit because it allows for greater articulation of the drive mechanism in the curved section 325 of the track 324.

A first end 301a of the drive mechanism 301 is configured to engage a drive spring (e.g., the spring 218 of FIG. 2), while the second end 301b of the drive mechanism is configured to engage a plunger (e.g., the plunger 208 of FIG.

2). Activation and operation of the drug delivery device 100 including the drive mechanism 301 of this embodiment may be substantially the same as described in relation to the embodiment of FIG. 2.

Figure 4A:
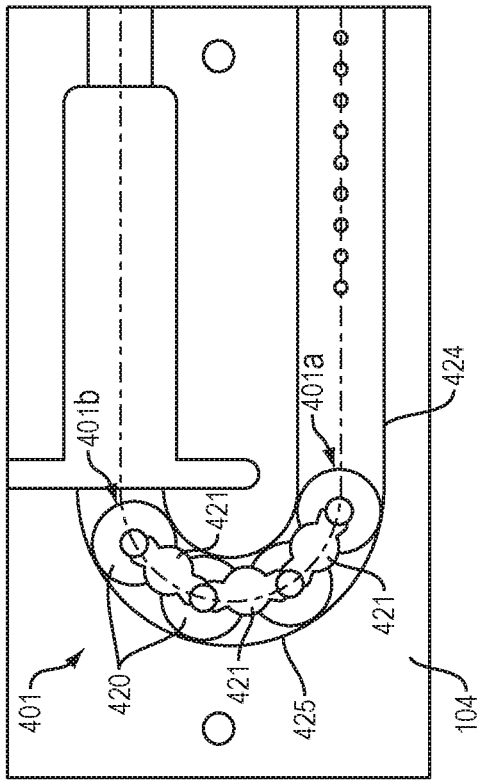
FIGS. 4A-4C illustrate an arrangement of force transfer elements for use with the drug delivery device of FIG. 1 in accordance with an embodiment of the present disclosure.
Figure 4B:
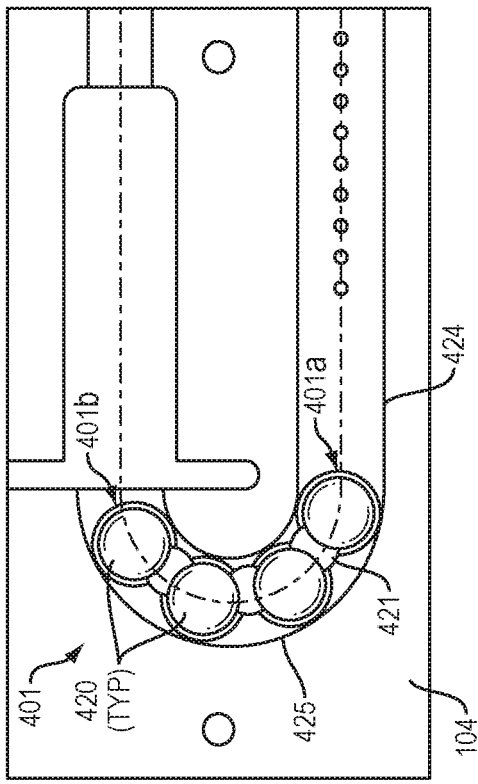
Figure 4C:
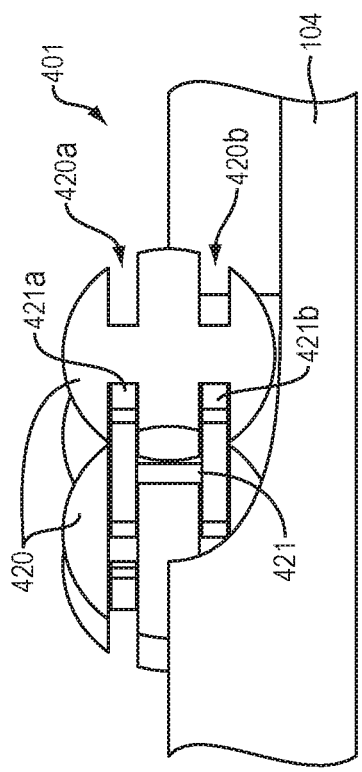

FIGS. 4A and 4B show a drive mechanism 401 with force transfer elements according to the present disclosure including a plurality of spherical rollers 420 disposed within a track 424 formed in or on the bottom 104 (FIG. 1) of the drug delivery device 100. Each spherical roller 420 includes first and second circumferential slots 420a, 420b for receiving first and second arms 421a, 421b of a spacer 421. The first and second circumferential slots 420a, 420b may be parallel, and may slindingly receive the first and second arms 421a, 421b of the spacer 421 to enable the spherical rollers 420 to rotate with respect to the spacer 421 and with respect to adjacent spherical rollers. This, in turn, enables the drive mechanism 401 to move through the curved section 425 of the track 424. An advantage of this embodiment is that the spacers 421 prevent the spherical roller 420 from touching each other on the large diameter, thus facilitating rolling movement of the rollers.

A first end 401a of the drive mechanism 401 is configured to engage a drive spring 218 (FIG. 2), while the second end 401b of the drive mechanism is configured to engage a plunger 208. Activation and operation of the drug delivery device 100 including the drive mechanism 401 of this embodiment may be substantially the same as described in relation to the embodiment of FIG. 2.

Figure 5A:
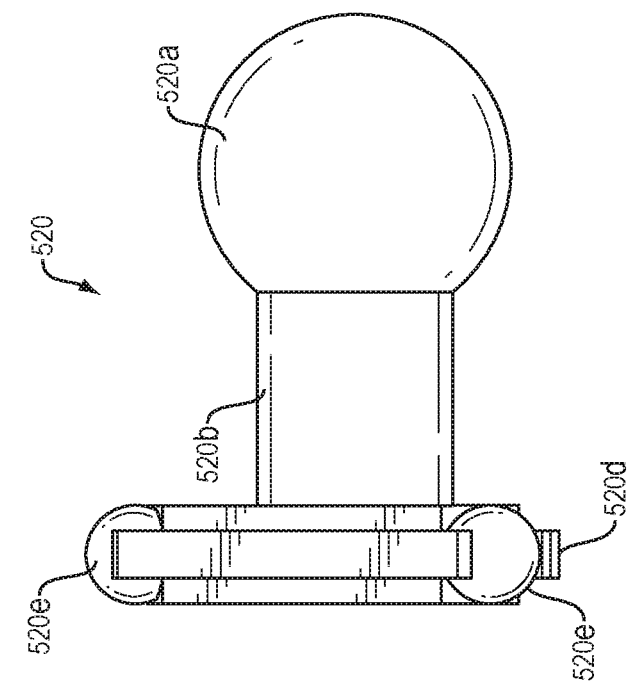
FIGS. 5A and 5B illustrate an arrangement of force transfer elements for use with the drug delivery device of FIG. 1 in accordance with an embodiment of the present disclosure.
Figure 5B:
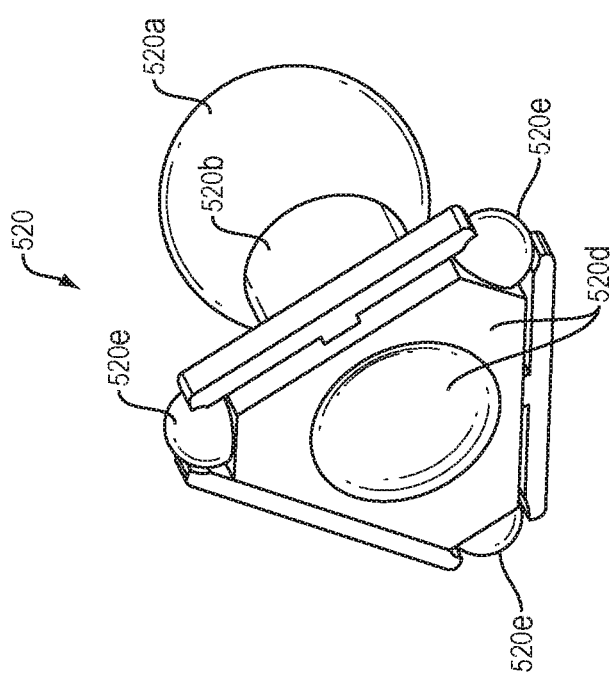

FIGS. 5A and 5B show a rolling ball link 520 of a drive mechanism with force transfer elements according to the present disclosure. Each rolling ball link 520 includes a partial spherical portion 520a, a neck portion 520b, and a base portion 520c. The base portions 520c of each rolling ball link 520 has a recess 520d therein for receiving the head portion 520a of an adjacent link. In some embodiments, the recess 520d may receive the head portion 520a of an adjacent link via a snap-fit. The recess 520d is sized and shaped to enable the received head portion 520a to pivot therein, thus allowing the individual links to pivot with respect to each other. Each base portion 520c can have a triangular shape, and can have a roller 520e rotatably disposed at each apex of the triangle. This enables the rollers 520e of each rolling ball link 520 to ride on the track and to spin. The rolling ball links 520 can be shorter than comparably sized spheres, thus allowing for more links in the curved section of the track. Such an arrangement can be a benefit because it allows for greater articulation of the drive mechanism in the curved section of the track.

Similar to other embodiments, a plurality of rolling ball links 520 can be coupled together to form a drive mechanism, which is configured to engage a drive spring 218 (FIG. 2) at one end, and to engage a plunger 208 at an opposite end. Activation and operation of the drug delivery device 100 including the plurality of rolling ball links 520 of this embodiment may be substantially the same as described in relation to the embodiment of FIG. 2.

Figure 6A:
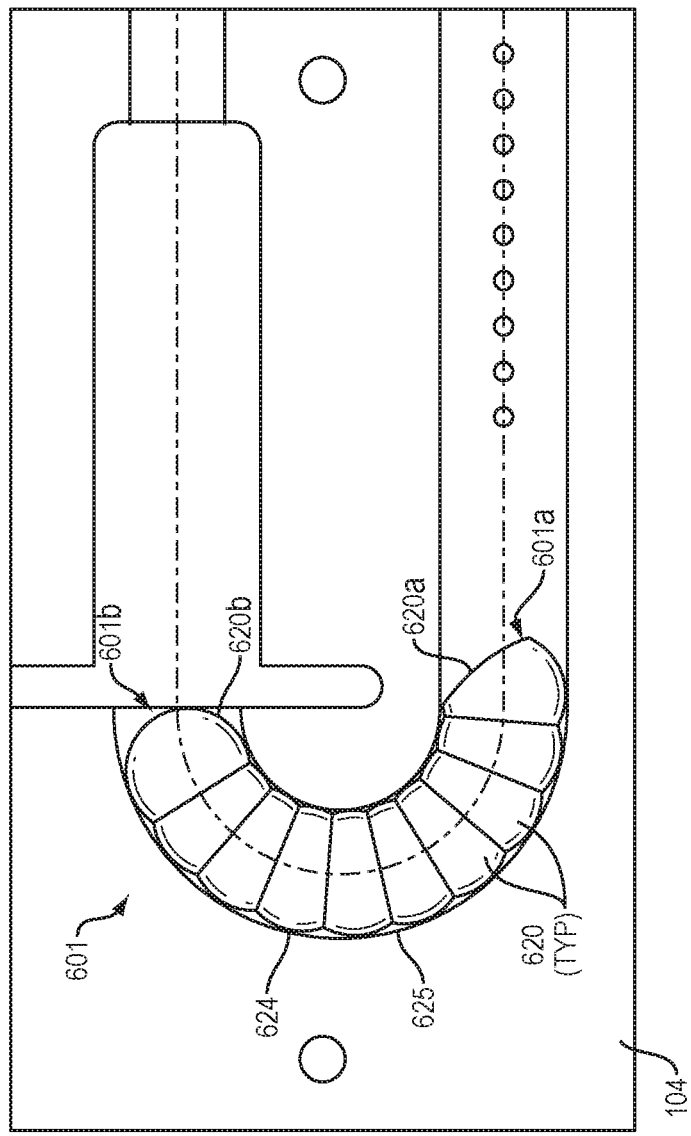
FIGS. 6A and 6B illustrates an arrangement of force transfer elements for use with the drug delivery device of FIG. 1 in accordance with an embodiment of the present disclosure.
Figure 6B:
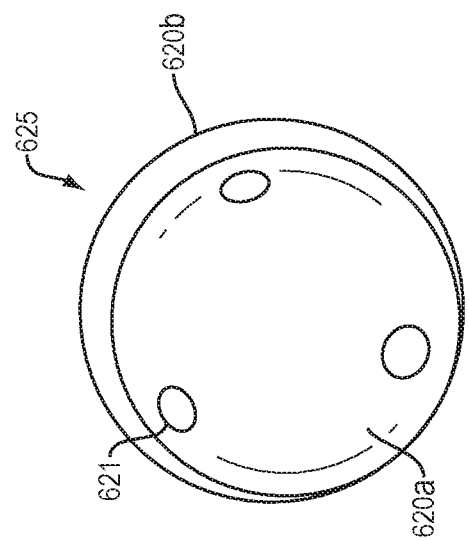

FIGS. 6A and 6B show a drive mechanism 601 with force transfer elements according to the present disclosure including a plurality of partial spherical rollers 620 disposed within a track 624 formed in or on the bottom 104 (FIG. 1) of the drug delivery device 100. Each partial spherical roller 620 includes a recess 620a for receiving the spherical portion 620b of an adjacent partial spherical roller 620 in the manner of a caterpillar. The nested arrangement of partial spherical rollers 620 allows the partial spherical rollers to rotate with respect to adjacent partial spherical rollers 620.

The nesting arrangement also means that the partial spherical rollers 620 can be shorter than comparably sized spheres, thus allowing for more links in the curved section 625 of the track. Such an arrangement can be a benefit because it allows for greater articulation of the drive mechanism 601 in the curved section 625 of the track 624.

In some embodiments, a plurality of bearings 621 can be disposed between the associated nested partial spherical rollers 620 to reduce friction between the recess 620a of one partial spherical roller and the spherical portion 620b of an adjacent roller.

A first end 601a of the drive mechanism 601 is configured to engage a drive spring 218 (FIG. 2), while the second end 601b of the drive mechanism is configured to engage a plunger 208. Activation and operation of the drug delivery device 100 including the drive mechanism 601 of this embodiment may be substantially the same as described in relation to the embodiment of FIG. 2.

FIGS. 7A and 7B show a roller bearing link 720 for a drive mechanism with force transfer elements according to the present disclosure where each link 720 includes a plurality of roller bearings 721. When viewed from the side/end, such as FIG. 7B, each of the roller bearings 721 may be disposed on or in a separate face 722 of the roller bearing link. In the illustrated embodiment, the faces are disposed 120-degrees apart from each other such that the roller bearing link 720 is supported at three points (i.e., at the three bearings). Each roller bearing link 720 may have a recess for receiving a pivot connector 723 to enable adjacent roller bearing links to pivot with respect to each other. The track 724 of this embodiment may include separately spaced rails 726 upon which the roller bearings 721 may run. In some embodiments, the rails 726 are disposed only in the curved section of the track, while in other embodiments the rails are employed along the entire length of the track.

Similar to other embodiments, a plurality of roller bearing links 720 can be coupled together to form a drive mechanism that is configured to engage a drive spring 218 (FIG. 2) at one end, and to engage a plunger 208 at an opposite end. Activation and operation of the drug delivery device 100 including the plurality of roller bearing link 720 of this embodiment may be substantially the same as described in relation to the embodiment of FIG. 2.

Figure 8A:
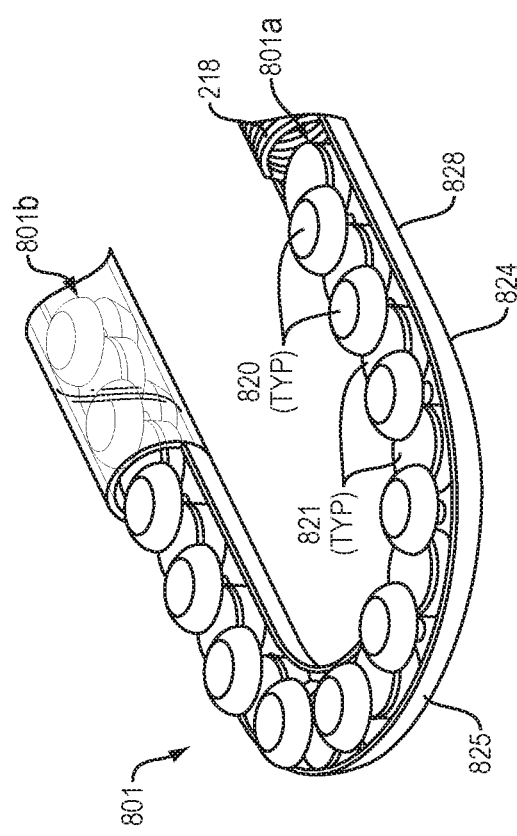
FIGS. 8A and 8B illustrate an arrangement of force transfer elements for use with the drug delivery device of FIG. 1 in accordance with an embodiment of the present disclosure.
Figure 8B:
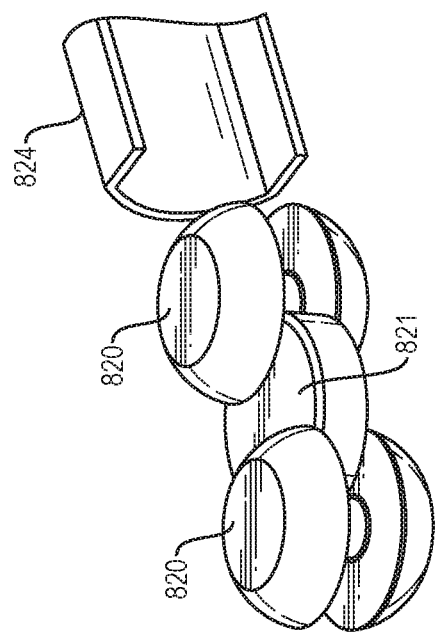

FIGS. 8A and 8B show a drive mechanism 801 with force transfer elements according to the present disclosure including a plurality of spherical rollers 820 disposed within a track 824 formed in or on the bottom 104 (FIG. 1) of the drug delivery device 100. Each spherical roller 820 includes a central circumferential slot 820a for receiving a portion of a disc spacer 821. The circumferential slot 820a may slindingly receive the disc spacer 821 to enable the spherical rollers 820 to rotate with respect to the disc spacer 821 and with respect to adjacent spherical rollers. This, in turn, enables the drive mechanism 801 to move through the curved section 825 of the track 824. An advantage of this embodiment is that the disc spacers 821 prevent the spherical rollers 820 from touching each other on the large diameter, thus facilitating rolling movement of the rollers. Another advantage is that the disc spacers 821 prevent the spherical rollers 820 from rotating in directions other than that which facilitates movement of the drive mechanism 801 along the track 824.

A first end 801a of the drive mechanism 801 is configured to engage a drive spring 218 (FIG. 2), while the second end 801b of the drive mechanism is configured to engage a plunger 208. Activation and operation of the drug delivery device 100 including the drive mechanism 801 of this embodiment may be substantially the same as described in relation to the embodiment of FIG. 2.

Figure 9A:
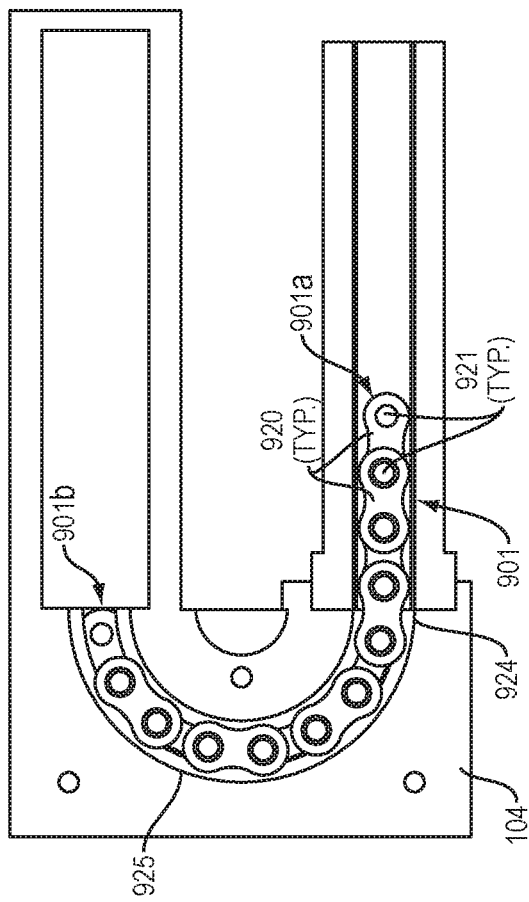
FIGS. 9A and 9B illustrate an arrangement of force transfer elements for use with the drug delivery device of FIG. 1 in accordance with an embodiment of the present disclosure.
Figure 9B:
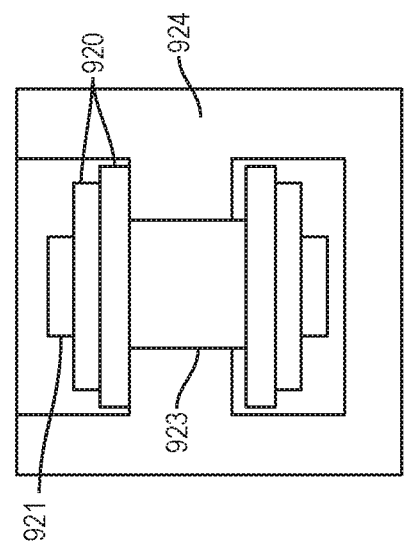

FIGS. 9A and 9B show a drive mechanism 901 with force transfer elements according to the present disclosure comprising a roller chain having individual chain links 920 disposed within a track 924 formed in or on the bottom 104 (FIG. 1) of the drug delivery device 100. Each chain link 920 is rotatably coupled to an adjacent chain link 920 via a pin 921, which enables the chain links 920 to rotate with respect to the pin 921 and with respect to adjacent chain links 920. Each pin 921 includes a cylindrical hollow body roller 923 about the pin 921 and between the chain links 920. The rollers 923 make contact with the track 924 and may spin about their respective pin 921 while the chain links 920 separate the pins 921 and keep the rollers 923 from contacting each other and allow the rollers 923 to roll. This, in turn, enables the drive mechanism 901 to move through the curved section 925 of the track 924.

A first end 901a of the drive mechanism 901 is configured to engage a drive spring 218 (FIG. 2), while the second end 901b of the drive mechanism is configured to engage a plunger 208. Activation and operation of the drug delivery device 100 including the drive mechanism 901 of this embodiment may be substantially the same as described in relation to the embodiment of FIG. 2.

FIG. 10 shows a drive mechanism 1001 with force transfer elements according to the present disclosure including a plurality of split sphere elements 1020 disposed within a track 1024 formed in or on the bottom 104 (FIG. 1) of the drug delivery device 100. Each split sphere element 1020 includes first and second shells 1020a, 1020b with an expanding element 1021, such as a spring, disposed therebetween biasing the first and second shells apart. This arrangement enables the entire track 1024 to be filled with expanding split sphere elements 1020, as opposed to a single long spring (such as might be used with a single-spring arrangement). The disclosed arrangement of split sphere elements 1020 can make the drive mechanism 1001 compliant through the curved section 1025 of the track 1024.

A first end 1001a of the drive mechanism 1001 is configured to engage a drive spring 218 (FIG. 2), while the second end 1001b of the drive mechanism is configured to engage a plunger 208. Activation and operation of the drug delivery device 100 including the drive mechanism 1001 of this embodiment may be substantially the same as described in relation to the embodiment of FIG. 2. Alternatively, the drive mechanism 1001 may partially or completely replace the need for a drive spring (such as drive spring 218 of FIG. 2). Replacing the drive spring may lower the spring constant (often the "k" variable in the art) or average spring constant needed for the springs of the device.

Figure 11:
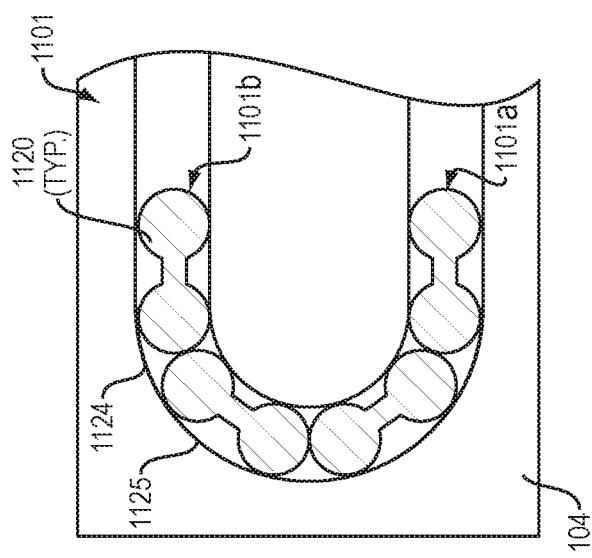
FIG. 11 illustrates an arrangement of force transfer elements for use with the drug delivery device of FIG. 1 in accordance with an embodiment of the present disclosure.

FIG. 11 shows a drive mechanism 1101 with force transfer elements according to the present disclosure including a plurality of dog bone shaped (i.e., wider ends than a thinner middle section connecting the wider ends) elements 1120 disposed within a track 1124 formed in or on the bottom 104 (FIG. 1) of the drug delivery device 100. Each dog bone shaped elements 1120 include first and second ends 1120a, 1120b connected by a neck portion 1120c. The diameter of the first and second ends 1120a, 1120b can be sized to slide within the track 1124. The diameter of the neck portion 1120c may be smaller than the diameter of the first and second ends 1120a, 1120b. The disclosed arrangement of dog bone shaped elements 1120 can reduce the total number of individual parts making up the drive mechanism 1101, while enabling the mechanism to be highly compliant through the curved section 1125 of the track 1124.

A first end 1101a of the drive mechanism 1101 is configured to engage a drive spring 218 (FIG. 2), while the second end 1101b of the drive mechanism is configured to engage a plunger 208. Activation and operation of the drug delivery device 100 including the drive mechanism 1101 of this embodiment may be substantially the same as described in relation to the embodiment of FIG. 2.

Figure 12:
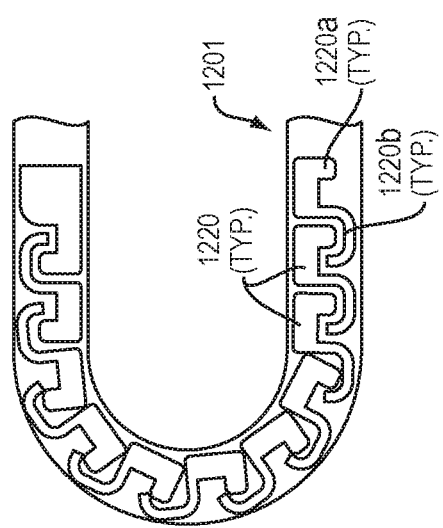
FIG. 12 illustrates an arrangement of force transfer elements for use with the drug delivery device of FIG. 1 in accordance with an embodiment of the present disclosure.

FIG. 12 shows a drive mechanism 1201 with force transfer elements according to the present disclosure comprising a plurality of inter-engaged custom link members 1220. Each custom link members 1220 includes a first end having a depending portion 1220a and a second end having a recess 1220b. The depending portion 1220a of one custom link member 1220 is configured to be received in the recess 1220b of a directly adjacent custom link member 1220. The depending portions 1220a may be rounded or spherical while the recesses 1220b may be sized and shaped to enable the received depending portion 1220a to pivot therein, thus allowing the individual links to pivot with respect to each other. The disclosed arrangement allows the drive mechanism 1201 to pivot the custom link members 1220 and articulate around the curved portion 225 of a guide track 224 (FIG. 2). The arrangement also enables the use of single-piece links 1220 that have the column strength of a chain, without the complexity and part count.

Similar to other embodiments, the drive mechanism 1201 can be disposed within an appropriate track 224 (FIG. 2), and can have first and second ends for engaging a drive spring 218 at one end, and to engage a plunger 208 at an opposite end. Activation and operation of the drug delivery device 100 including the plurality of custom link members 1220 of this embodiment may be substantially the same as described in relation to the embodiment of FIG. 2.

Figure 13:
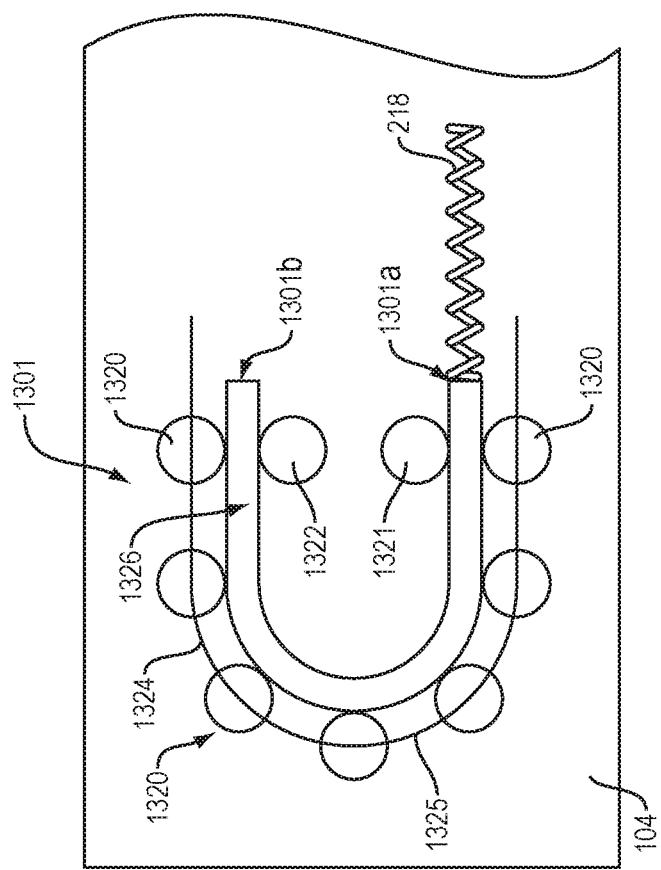
FIG. 13 illustrates an arrangement of force transfer elements for use with the drug delivery device of FIG. 1 in accordance with an embodiment of the present disclosure.

FIG. 13 shows a drive mechanism 1301 with force transfer elements according to the present disclosure including a plurality of spherical rollers 1320 engaged with a track 1324 formed in or on the bottom 104 (FIG. 1) of the drug delivery device 100. First and second spherical rollers 1321, 1322 oppose associated ones of the plurality of spherical rollers 1320 at each end of the curved portion 1325 of the track 1324. A flexible guide rod 1326 is guided through the track 1324 via the plurality of spherical rollers 1320. The flexible guide rod 1326 is constrained and guided into/out of the track 1324 via the first and second spherical rollers 1321, 1322.

The flexible guide rod 1326 can be sufficiently flexible to move through the curved section 1325 of the track 1324 while still maintaining a desired column strength to move the plunger 208 (FIG. 2). A first end 1301a of the drive mechanism 1301 is configured to engage a drive spring 218 (FIG. 2), while the second end 1301b of the drive mechanism is configured to engage a plunger 208. Activation and operation of the drug delivery device 100 including the drive mechanism 1301 of this embodiment may be substantially the same as described in relation to the embodiment of FIG. 2.

Figure 14:
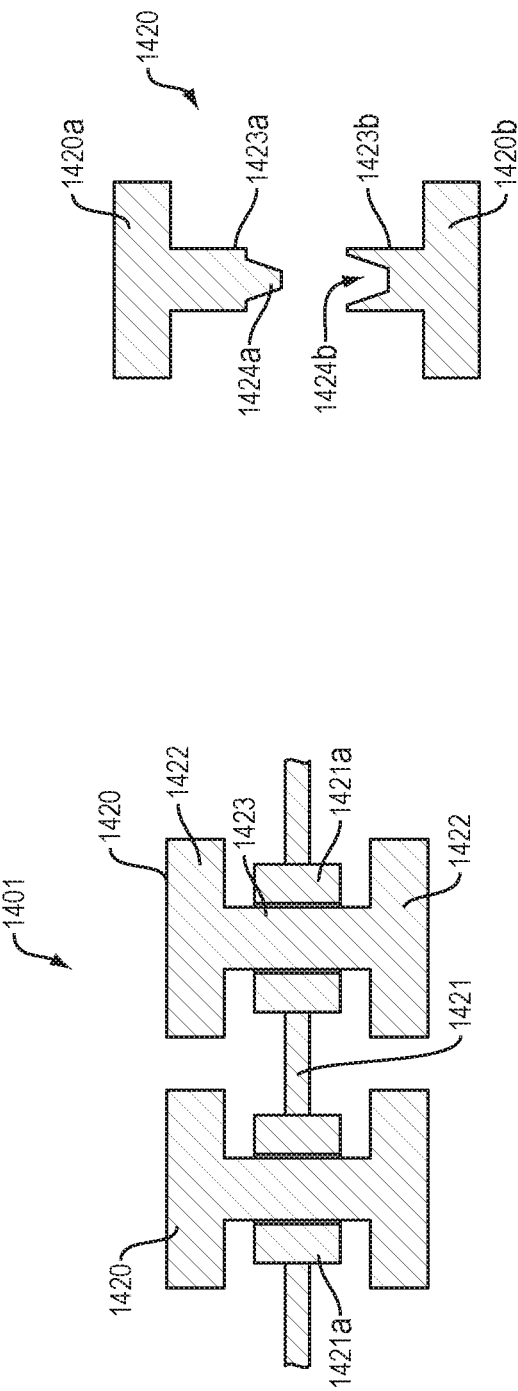
FIGS. 14A and 14B illustrate an arrangement of force transfer elements for use with the drug delivery device of FIG. 1 in accordance with an embodiment of the present disclosure.

FIGS. 14A and 14B show a drive mechanism 1401 with force transfer elements according to the present disclosure comprising a roller chain having a plurality individual chain links 1420, where adjacent chain links 1420 are coupled together by a bushed connecting link 1421. Each chain link 1420 can have first and second roller portions 1422 connected via a reduced-diameter portion 1423. The first and second roller portions 1422 can be sized to conform to the inner dimension of an associated guide track 224 (FIG. 2) so that they can ride on the walls of the guide track. The bushed connecting link 1421 can engage the reduced-diameter portions 1423 of adjacent chain links 1420. The bushed connecting link 1421 can couple to each of the reduced-diameter portions 1423 of adjacent chain links 1420 via a collar 1421*a* that allows the individual chain links 1420 to rotate with respect to the bushed connecting link 1421. The bushed connecting link 1421 may be stiff enough to transmit the spring force from the drive spring 218 (FIG. 2) to the plunger 208, while enabling the individual chain links 1420 to pivot with respect to each other. This, in turn, enables the drive mechanism 1401 to move through the curved section 225 (FIG. 2) of the track 224.

Similar to other embodiments, a plurality of chain links 1420 can be coupled together to form a drive mechanism 1401 that is configured to engage a drive spring 218 (FIG. 2) at one end, and to engage a plunger 208 at an opposite end. Activation and operation of the drug delivery device 100 including the plurality of chain links 1420 of this embodiment may be substantially the same as described in relation to the embodiment of FIG. 2.

FIG. 14B shows an example embodiment of how the individual chain links 1420 can be assembled from upper and lower portions 1420*a*, 1420*b*. The upper and lower portions 1420*a*, 1420*b* can have first and second reduced diameter portions 1423*a*, 1423*b*. In the illustrated embodiment the first reduced diameter portion 1423*a* includes a projection 1424*a* received within a recess 1424*b* in the second reduced diameter portion 1423*b*. The projection 1424*a* can be fixed within the recess 1424*b* using any of a variety of appropriate technologies, including press-fit, adhesives, threads, and the like. During assembly, the first and second reduced diameter portions would be engaged with each other within a collar 1421*a* of bushed connecting link 1421.

Figure 15:
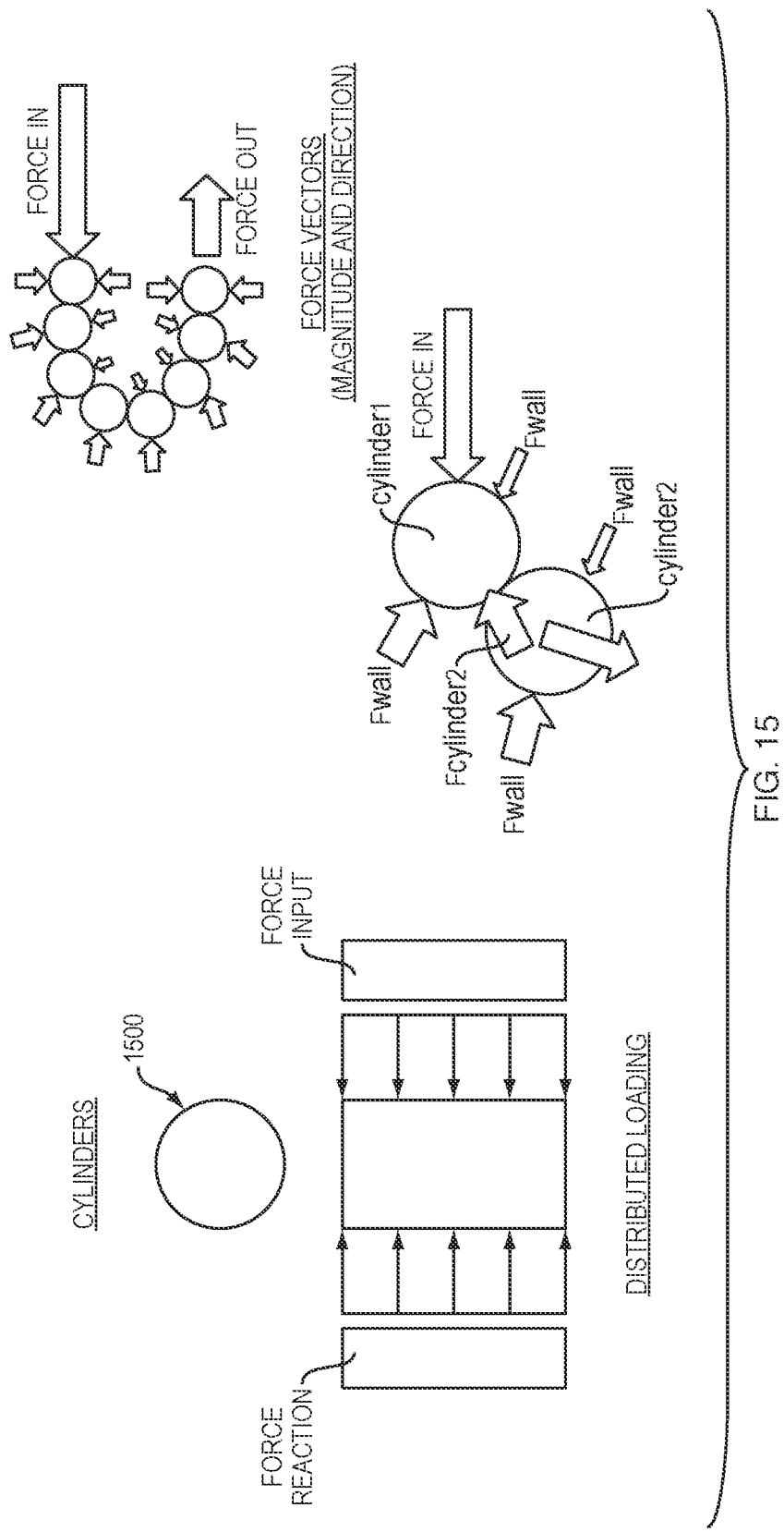
FIG. 15 illustrates an arrangement of force transfer elements for use with the drug delivery device of FIG. 1 in accordance with an embodiment of the present disclosure.

FIG. 15 shows an embodiment in which the force transfer elements according to the present disclosure comprise cylindrical elements 1500. In one embodiment the cylinders 1500 may be roller pins, which can maximize the transfer of loads, while minimizing deformation of the pin or its opposing surfaces. Input forces (from the drive spring 218 (FIG. 2)) will not equal output forces, due to losses in friction around the curved portion 225 of the track 224. Minimizing point loading and deformation, however, will tend to provide the highest output forces (i.e., highest efficiency). Providing the force transfer elements as cylindrically shaped elements 1500 allows for a plurality of elements to transfer the maximum force vector while minimizing losses and conforming to the track 224 within the drug delivery device 100 without buckling.

Figure 16:
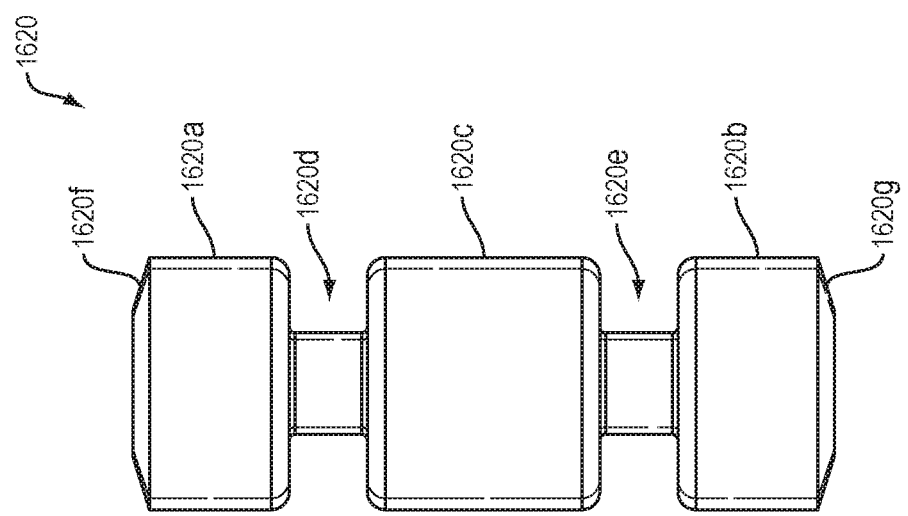
FIG. 16 illustrates an arrangement of force transfer elements for use with the drug delivery device of FIG. 1 in accordance with an embodiment of the present disclosure.

FIG. 16 shows an exemplary cylindrical force transfer element 1620 for a drive mechanism with force transfer elements according to the present disclosure. The force transfer element 1620 may have top and bottom portions 1620*a*, 1620*b* and a central portion 1620*c*. First and second reduced diameter portions 1620*d*, 1620*e* may be located between the top and central portions 1620*a*, 1620*c* and the bottom and central portions 1620*b*, 1620*c*, respectively. The top and bottom portions 1620*a*, 1620*b* may include beveled upper/lower surfaces 1620*f*, 1620*g* to reduce the surface area that will contact surfaces of the track 224 (FIG. 2). The first and second reduced diameter portions 1620*d*, 1620*e* may receive rail or other protruding features of the track 224 to guide and support the cylindrical force transfer elements 1620 within the straight portions of the track (e.g., where the spring 218 extends).

Similar to other embodiments, a plurality of cylindrical force transfer elements 1620 can be coupled together to form a drive mechanism that is configured to engage a drive spring 218 (FIG. 2) at one end, and to engage a plunger 208 at an opposite end. Activation and operation of the drug delivery device 100 including the plurality of cylindrical force transfer elements 1620 of this embodiment may be substantially the same as described in relation to the embodiment of FIG. 2.

Figure 17:
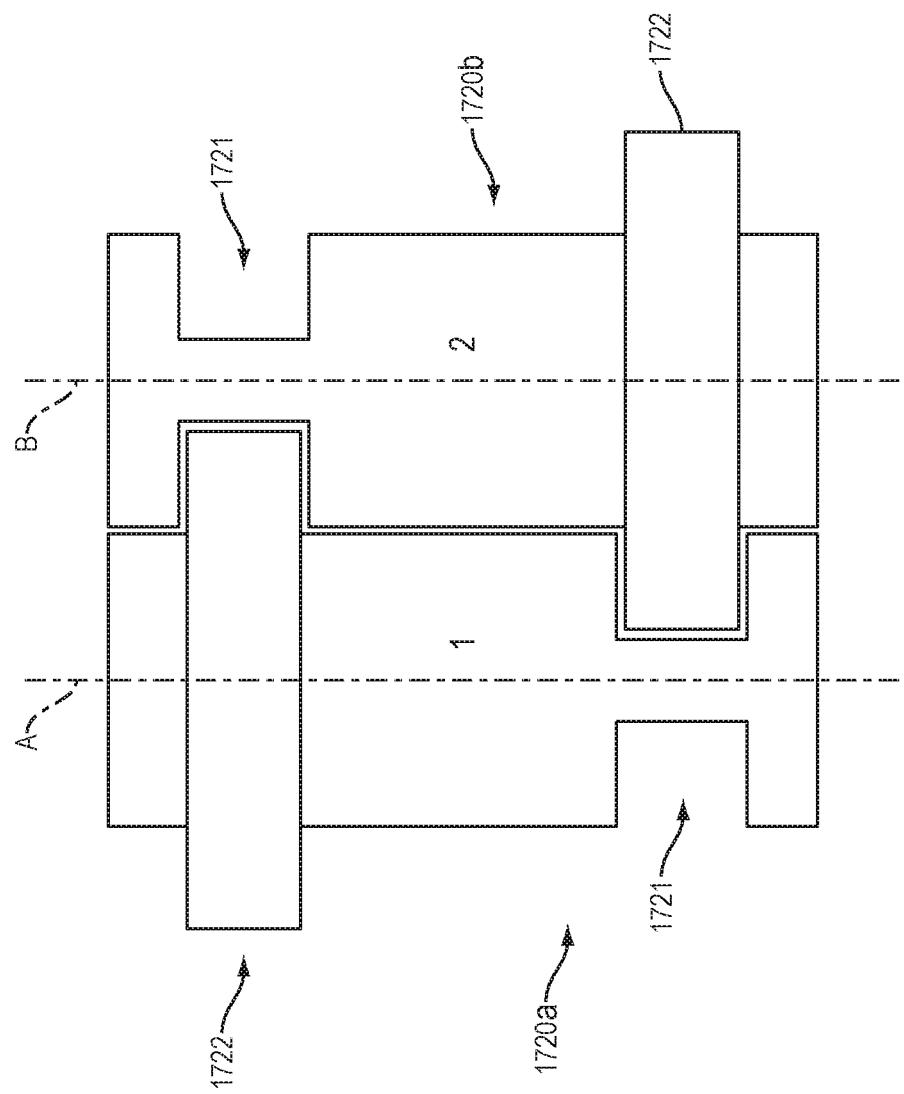
FIG. 17 illustrates an arrangement of force transfer elements for use with the drug delivery device of FIG. 1 in accordance with an embodiment of the present disclosure.

FIG. 17 shows a pair of exemplary cylindrical force transfer elements 1720*a*, 1720*b* for a drive mechanism with force transfer elements according to the present disclosure which include keying features that allow the elements 1720*a*, 1720*b* to couple together while also allowing them to rotate with respect to each other (e.g., when traversing the curved portion 225 of the track 224 (FIG. 2). As can be seen, the cylindrical force transfer elements 1720*a*, 1720*b* are 180-degree rotated images of each other. Each of the force transfer elements 1720*a*, 1720*b* includes a circumferential recess 1721 and a circumferential projection 1722. The recess 1721 and projection 1722 are sized and positioned so that the projection is received within the recess 1721 when the force transfer elements 1720*a*, 1720*b* are coupled together.

The projection 1722 may be loosely received within the recess 1721 to enable the force transfer elements 1720*a*, 1720*b* to rotate about their respective longitudinal axes A-A, B-B and to rotate with respect to each other about axes parallel to their longitudinal axes. This will enable the force transfer elements 1720*a*, 1720*b* to traverse the curved portion 225 of the track 224 of the drug delivery device 100. The interaction of the projection 1722 and recess 1721 may, however, prevent rotation of the force transfer elements 1720*a*, 1720*b* about other axes. Thus, the cylindrical force transfer elements 1720*a*, 1720*b* of this embodiment will not randomly "fan-out" or twist within the track 224 of the drug delivery device 100. Rather, they will be rotationally constrained from the cylinders that remain in the track.

Figure 18:
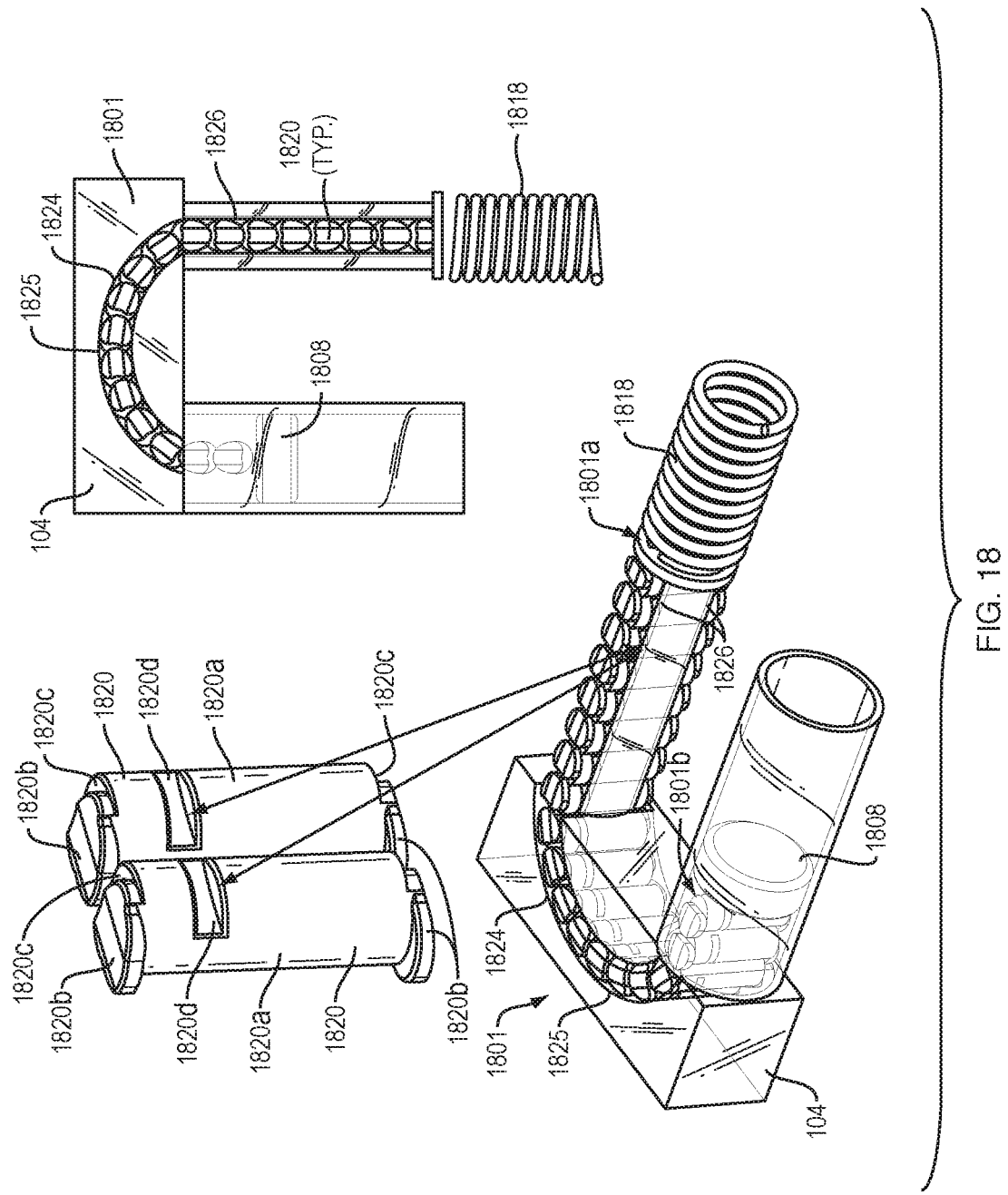
FIG. 18 illustrates an arrangement of force transfer elements for use with the drug delivery device of FIG. 1 in accordance with an embodiment of the present disclosure.
Figure 19C:
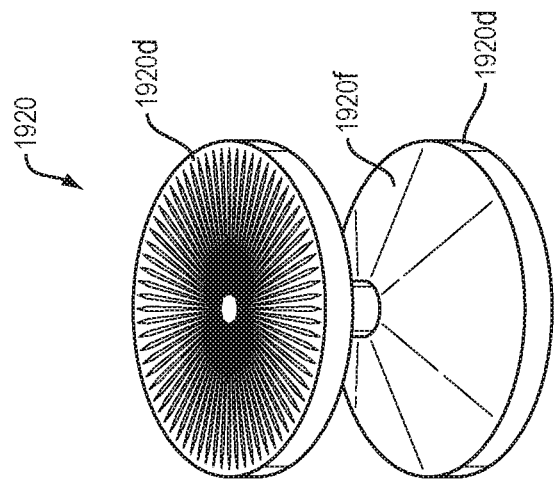
FIGS. 19A-19C illustrate an arrangement of force transfer elements for use with the drug delivery device of FIG. 1 in accordance with an embodiment of the present disclosure.
Figure 19B:
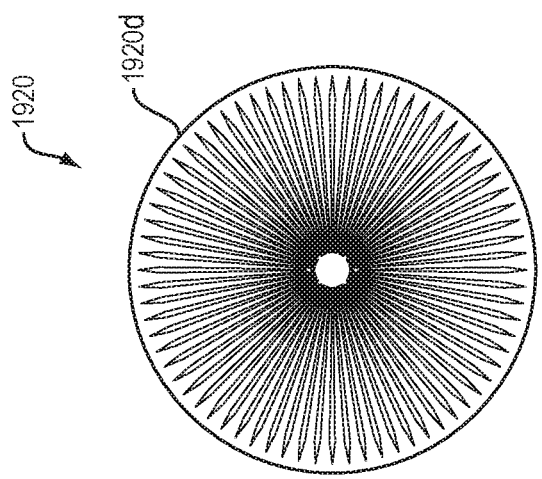
Figure 19A:
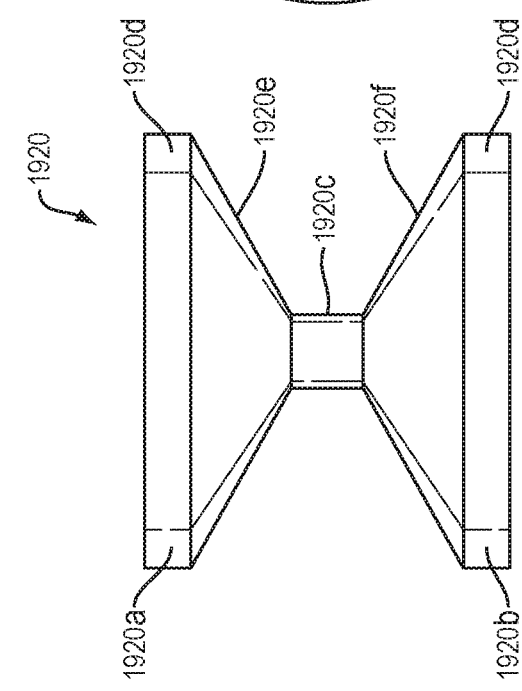

FIG. 18 shows an embodiment of a drive mechanism 1801 for a drive mechanism with force transfer elements according to the present disclosure including a plurality of cylindrical force transfer elements 1820 disposed within a track 1824 formed in or on the bottom 104 (FIG. 1) of the drug delivery device 100. Each cylindrical force transfer elements 1820 includes a cylindrical body portion 1820*a*, and offset top and bottom portions 1820*b*. Adjacent the offset top and bottom portions 1820*b* are recess portions 1820*c*. The recess portions 1820*c* are configured to slidingly engage respective offset top and bottom portions 1820*b* of an adjacent cylindrical force transfer element 1820. This overlapping engagement allows adjacent cylindrical force transfer element 1820 to move with respect to each other as the drive mechanism 1801 traverses the curved portion 1825 of the track 1824, while preventing them from "fanning-out," over-rotating with respect to each other, or twisting within the track 1824 of the drug delivery device 100.

Each of the plurality of cylindrical force transfer elements 1820 may also include one or more grooves 1820*d* disposed in the cylindrical body portion 1820*a*. These grooves 1820*d* may be oriented so that they are parallel to the bottom 104 of the drug delivery device. 100. The grooves 1820*d* may be sized and shaped to interface with guide rails 1826 disposed on one or more surfaces of the track 1824. In the illustrated embodiment, the guide rails 1826 are disposed in a straight portion of the track 1824 adjacent to the drive spring 1818. In other embodiments, the rails may be disposed in the curved portion of the track in addition to the straight portion.

A first end 1801*a* of the drive mechanism 1801 is configured to engage a drive spring 1818, while the second end 1801*b* of the drive mechanism is configured to engage a plunger 1808. Activation and operation of the drug delivery device 100 including the drive mechanism 1801 of this embodiment may be substantially the same as described in relation to the embodiment of FIG. 2.

FIGS. 19A-23 show a drive mechanism with force transfer elements according to the present disclosure in which the force transfer elements are designed as constant angular velocity force transfer rollers 1920. The force transfer rollers 1920 have an hourglass shape in profile, and include upper and lower portions 1920a, 1920b coupled by a reduced diameter portion 1920c. Each of the upper and lower portions 1920a, 1920b has a cylindrical portion 1920d, which tapers to the reduced diameter portion 1920c resulting in upper and lower angled transition portions 1920e, 1920f The top and/or bottom surfaces of the cylindrical portions 1920d include an array of radial etching markers even spaced about a center point of the cylindrical portions 1920d. The etchings provide visual indication of motion of the rollers 1920 that may be measurable (e.g., a number of marks rotating and/or translating along a track).

FIGS. 20A and 20B show a track 2024 for use with the force transfer rollers 1920. The track 2024 may be generally U-shaped, comprising a pair of straight track portions 2024a, 2024b and an intermediate curved track portion 2025. The inner walls of the straight track portions 2024a, 2024b and the outer track wall of the curved track portion 2025 may be flat. The inner track wall of the curved track portion 2025 may have an expanded radius "R" and a tapered cross-section that produces a reduced-thickness portion 2025a at the perimeter of the inner track wall of the curved track portion. The substantially U-shaped track 2024 includes the straight track portions 2024a, 2024b with walls spaced apart from each other a first distance, and a curved track portion 2025 with walls spaced apart from each other a second distance that is smaller than the first distance.

Figure 21:
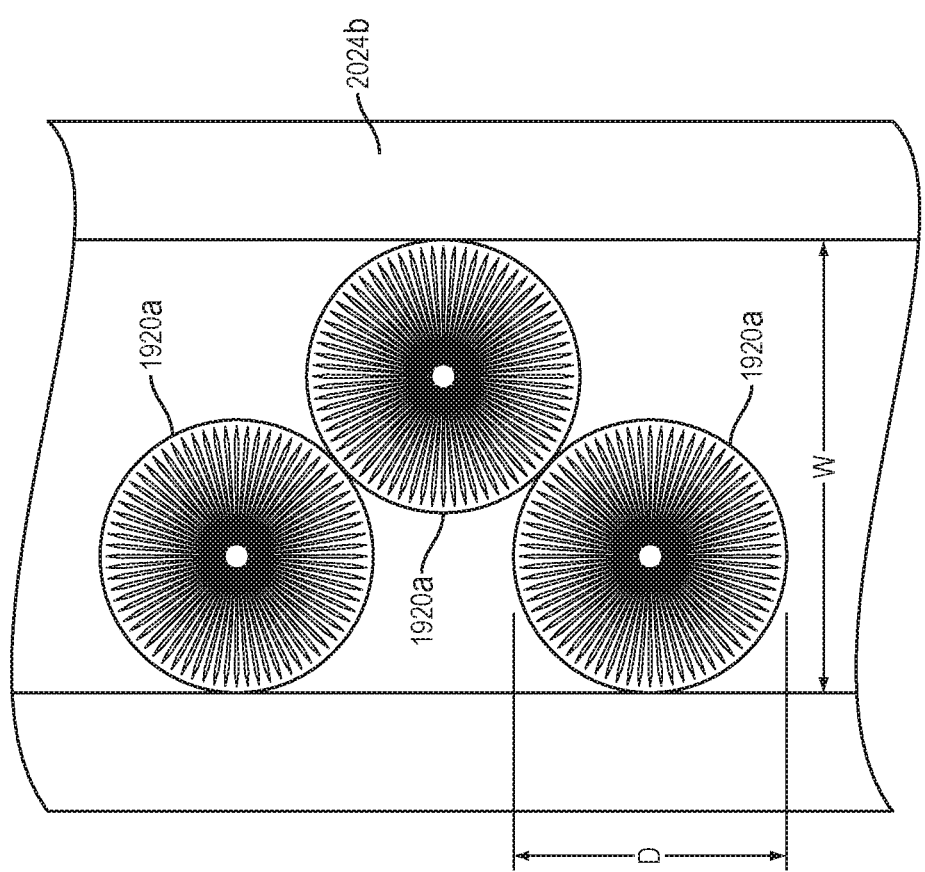
FIGS. 21-23 illustrate the force transfer elements of FIGS. 19A-19C at first, second and third states of operation, respectively, in accordance with an embodiment of the present disclosure.

FIG. 21 shows the configuration of the force transfer rollers 1920 while they are in the straight portion 2024b (or 2024a) of the track 2024. While the force transfer rollers 1920 are in the straight portion of the track they all roll on the largest radius portions (i.e., upper and lower portions 1920a, 1920b). As can be seen, the upper and lower portions 1920a, 1920b have diameters "D" that are smaller than a width "W" of the track 2024. The force transfer rollers 1920 thus adjust their relative positions to fit within the track 2024, creating a double stack arrangement. In the straight portion of the track, both stacks of rollers are rolling on equal radii. The ability to roll comes from the double stack design and avoids forced sliding that can occur in a single stack arrangement.

Figure 22:
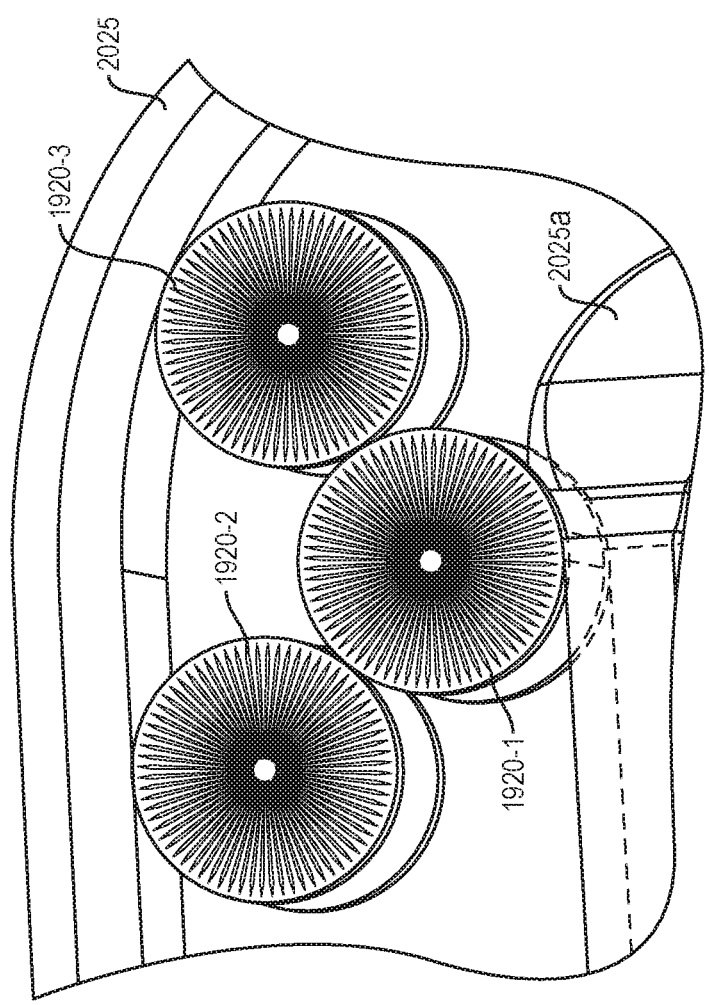

FIG. 22 shows the positions of the force transfer rollers 1920 in a transition region between the straight portion 2024a/2024b and the curved portion 2025. The rollers in the inside stack (1920-1) will roll on a non-constant radius surface 2025a to maintain contact with the rollers in the outside stack (1920-2, 1920-3). While the rollers are going through the transition area they will roll on the angled transition portion 1920f (FIG. 19A), bringing the radius down from to the final size before rolling in the curved section 2025.

In order to transition from the known straight configuration to the known curved section 2025 there must be a transition where the radius of the force transfer rollers 1920 changes with angular distance travelled until the rollers reach the curved section of the track. Entering the curved section 2025 may cause the force transfer rollers 1920 to slip instead of roll if the geometry between rollers changes. As can be seen, the angle between rollers is smaller when they are travelling in the straight portion than when they are in the curved portion. The transition curve may need both the inner and outer stacks to have different, changing radii at the same time to maintain 100% rolling. In some embodiments, the angled transition portion 1920f (FIG. 19A) may not be a straight line, but rather may be a radius change as defined by a curve.

Figure 23:
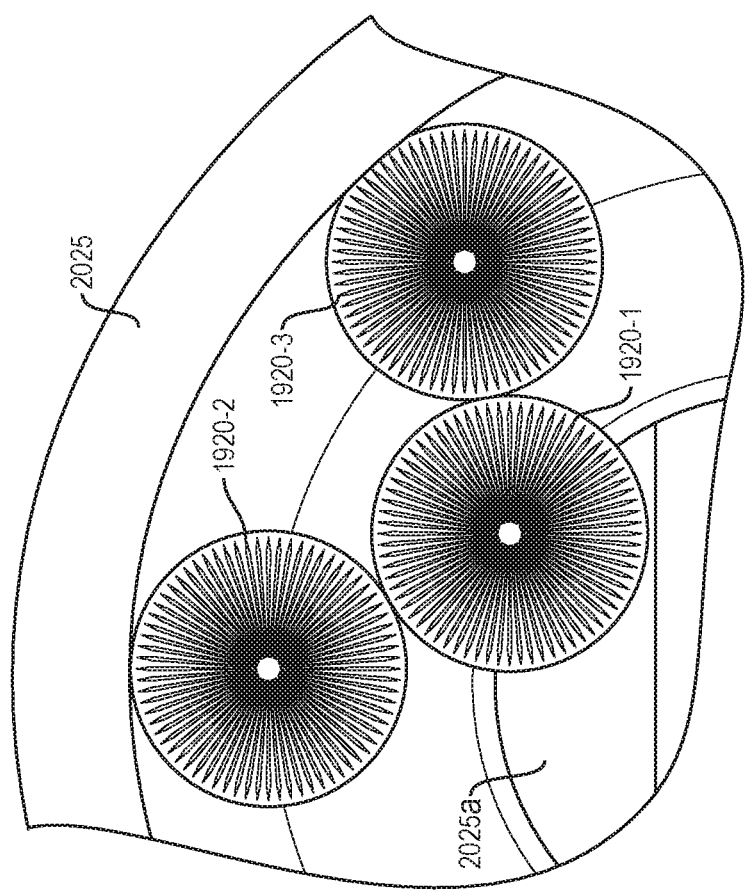

FIG. 23 shows the rollers 1920 in the curved portion of the track 2025. As can be seen, the inner stack (1920-1) rolls on the smallest radius to maintain a constant linear velocity relative to the rollers in the outside stack (1920-2, 1920-3). There is a known but different configuration in the curved part of the track 2025 where the inside stack is rolling on the smallest radius (i.e., the reduced diameter portion 1920-c (FIG. 19A) and the outside stack rolls on the largest radii (cylindrical portions 1920d). The ratio between radii is equal to the ratio between track radii.

With the embodiment of FIGS. 19A-23, the force transfer rollers 1920 in both stacks should satisfy v=ωr (with v being tangential linear velocity, ω being angular velocity, and r being the radius), where v is constant and equal for both stacks. In the straight sections (2024a, 2024b) this is achieved by having equal radii and an equal linear distance. In the curved portion 2025, the outside track has a larger linear distance, so the rollers must change radius to compensate. Either the outer stack of rollers (1920-2, 1920-3) need a larger rolling radius (i.e., UFO shape) or the inner stack of rollers (1920-1) needs a smaller rolling radius (i.e., hourglass). The track 2024 should include a variable radius portion (2025a) to meet the roller and facilitate rolling at the appropriate radius for that point in the transition.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A drug delivery device, comprising:
a drug container for storing a liquid drug, a first end of the drug container sealed by a plunger;
a needle conduit coupled to the plunger;
a needle insertion component coupled to the needle conduit; and
a drive mechanism coupled to the plunger, the drive mechanism including a drive spring and a plurality of substantially cylindrical force transfer elements, wherein each substantially cylindrical force transfer element of the plurality of substantially cylindrical force transfer elements has a longitudinal axis that is both offset and parallel at once to the longitudinal axis of an adjacent one of the plurality of substantially cylindrical force transfer elements, and the plurality of substantially cylindrical force transfer elements are physically distinct from one another.

2. The drug delivery device of claim 1, wherein each of the plurality of substantially cylindrical force transfer elements further comprises:
a rail-engaging groove in a cylindrical body portion, configured to engage a rail disposed on a sidewall of a track of the drug delivery device.

3. The drug delivery device of claim 1, wherein the drive mechanism comprises:
a first end configured to engage the drive spring.

4. The drug delivery device of claim 3, wherein the drive mechanism further comprises:
a second end configured to engage the plunger, wherein the second end is a substantially cylindrical force transfer element of the plurality of substantially cylindrical force transfer elements.

5. The drug delivery device of claim 1, wherein each of the plurality of substantially cylindrical force transfer elements includes:
a cylindrical body portion; and
a groove disposed in the cylindrical body portion, wherein the groove is oriented to be parallel to an offset portion of a respective substantially cylindrical force transfer element of the plurality of substantially cylindrical force transfer elements.

6. The drug delivery device of claim 1, further comprising:
a track formed in or on a bottom of the drug delivery device, wherein:
the plurality of substantially cylindrical force transfer elements are disposed within the track, and
each of the plurality of substantially cylindrical force transfer elements includes a groove sized and shaped to interface with a guide rail of the track.

7. The drug delivery device of claim 6, wherein the track further comprises:
a straight portion and a curved portion, and
the guide rail is disposed in the straight portion.

8. The drug delivery device of claim 6, wherein the track further comprises:
a straight portion and a curved portion, and
the guide rail is disposed in the straight portion and the curved portion.

9. The drug delivery device of claim 1, wherein each substantially cylindrical force transfer element of the plurality of substantially cylindrical force transfer elements further includes a cylindrical body portion, a bottom recess portion and an offset portion of each substantially cylindrical force transfer element of the plurality of substantially cylindrical force transfer elements is a bottom offset portion, wherein the bottom offset portion of each substantially cylindrical force transfer element of the plurality of substantially cylindrical force transfer elements:
extends beyond the cylindrical body portion, and
is configured to slidingly engage a corresponding bottom recess portion of an immediately adjacent respective substantially cylindrical force transfer element of the plurality of substantially cylindrical force transfer elements.

10. A drug delivery device, comprising:
a drug container for storing a liquid drug, a first end of the drug container sealed by a plunger;
a needle conduit coupled to the plunger;
a needle insertion component coupled to the needle conduit; and
a drive mechanism coupled to the plunger, the drive mechanism including a drive spring and a plurality of substantially cylindrical force transfer elements, wherein the plurality of substantially cylindrical force transfer elements are physically distinct from one another and each substantially cylindrical force transfer element of the plurality of substantially cylindrical force transfer elements has a longitudinal axis that is offset and parallel at all times to the longitudinal axis of an adjacent one of the plurality of substantially cylindrical force transfer elements, and each substantially cylindrical force transfer element of the plurality of substantially cylindrical force transfer elements includes:
a cylindrical body portion, an offset portion and a recess portion, wherein the offset portion extends beyond the cylindrical body portion and is configured to directly and slidingly engage a corresponding recess portion of the adjacent one of the plurality of substantially cylindrical force transfer elements.

11. The drug delivery device of claim 10, wherein the drive mechanism further comprises:
a second end configured to engage the plunger, wherein the second end is a substantially cylindrical force transfer element of the plurality of substantially cylindrical force transfer elements.

12. The drug delivery device of claim 10, wherein each physically distinct, substantially cylindrical force transfer element of the plurality of substantially cylindrical force transfer elements has a top base, and
each physically distinct, substantially cylindrical force transfer element of the plurality of substantially cylindrical force transfer elements further includes:
a groove disposed in a curved face of the cylindrical body portion, wherein the groove is oriented to be parallel to the top base of each substantially cylindrical force transfer element of the plurality of substantially cylindrical force transfer elements.

13. The drug delivery device of claim 10, further comprising:
a track formed in or on a bottom of the drug delivery device, wherein:
the plurality of substantially cylindrical force transfer elements are disposed within the track, and
each of the plurality of substantially cylindrical force transfer elements includes a groove sized and shaped to interface with a guide rail of the track.

14. The drug delivery device of claim 13, wherein the track further comprises:
a straight portion and a curved portion, and
the guide rail is disposed in the straight portion.

15. The drug delivery device of claim 13, wherein the track further comprises:
a straight portion and a curved portion, and
the guide rail is disposed in the straight portion and the curved portion.

16. A drug delivery device, comprising:
a drug container for storing a liquid drug, a first end of the drug container sealed by a plunger;
a needle conduit coupled to the plunger, wherein the needle conduit includes a needle that is operable to pierce the plunger;
a needle insertion component coupled to the needle conduit; and
a drive mechanism coupled to the plunger, the drive mechanism including a drive spring and a plurality of substantially cylindrical force transfer elements, wherein a curved face of one substantially cylindrical force transfer element of the plurality of substantially cylindrical force transfer elements is oriented vertically and directly adjacent to a curved face of an adjacent substantially cylindrical force transfer element of the plurality of substantially cylindrical force transfer elements.

17. The drug delivery device of claim 16, wherein each of the plurality of substantially cylindrical force transfer elements further comprises:
   a rail-engaging groove in a cylindrical body portion, configured to engage a rail disposed on a sidewall of a track of the drug delivery device.

18. The drug delivery device of claim 16, wherein the drive mechanism comprises:
   a first end configured to engage the drive spring.

19. The drug delivery device of claim 18, wherein the drive mechanism further comprises:
   a second end configured to engage the plunger, wherein the second end is a substantially cylindrical force transfer element of the plurality of substantially cylindrical force transfer elements.

20. The drug delivery device of claim 16, further comprising:
   a track formed in or on a bottom of the drug delivery device, wherein:
      the plurality of substantially cylindrical force transfer elements are disposed within the track, and
      each of the plurality of substantially cylindrical force transfer elements includes a groove sized and shaped to interface with a guide rail of the track.

* * * * *